(12) United States Patent
Schütze et al.

(10) Patent No.: US 10,545,091 B2
(45) Date of Patent: Jan. 28, 2020

(54) DEVICE AND METHOD FOR ANALYZING BIOLOGICAL OBJECTS WITH RAMAN SPECTROSCOPY

(71) Applicant: CellTool GmbH, Bernried (DE)

(72) Inventors: Karin Schütze, Tutzing (DE); Raimund Schütze, Tutzing (DE)

(73) Assignee: CellTool GmbH, Bernried (DE)

( * ) Notice: Subject to any disclaimer, the term of this patent is extended or adjusted under 35 U.S.C. 154(b) by 0 days.

(21) Appl. No.: 15/778,116

(22) PCT Filed: Nov. 23, 2016

(86) PCT No.: PCT/EP2016/078599
§ 371 (c)(1),
(2) Date: May 22, 2018

(87) PCT Pub. No.: WO2017/089427
PCT Pub. Date: Jun. 1, 2017

(65) Prior Publication Data
US 2018/0348137 A1    Dec. 6, 2018

(30) Foreign Application Priority Data
Nov. 23, 2015 (DE) .......... 10 2015 223 080

(51) Int. Cl.
*G01J 3/44* (2006.01)
*G01N 21/65* (2006.01)
(Continued)

(52) U.S. Cl.
CPC ............ *G01N 21/65* (2013.01); *G01N 21/03* (2013.01); *G01N 33/5014* (2013.01);
(Continued)

(58) Field of Classification Search
CPC ........ G01N 21/64; G01N 21/65; G01N 21/62; G01N 21/55; G01N 21/47; G01N 21/59;
(Continued)

(56) References Cited

U.S. PATENT DOCUMENTS 6,485,413 B1 * 11/2002 Boppart ............. A61B 1/00096
356/450
2002/0030811 A1   3/2002 Schindler
2005/0123917 A1   6/2005 Labischinski et al.
2008/0094624 A1 * 4/2008 Harsh ...................... G01J 3/02
356/311
2009/0010388 A1   1/2009 Stahly
(Continued)

FOREIGN PATENT DOCUMENTS

DE    102011008788    5/2012
WO    2012033409      3/2012

OTHER PUBLICATIONS

Ing-Ting Liu et al: "A High Speed Detection Platform Based on Surface-Enhanced Raman Scattering for Monitoring Antibiotic-Induced Chemical Changes in Bacteria Cell Wall", PLOS ONE, vol. 4, No. 5, May 2009 (May 2009), XP055087067, ISSN: 1932-6203, DOI: 10.1371/journal.pone.0005470 abstract; figures 4-5 p. 4 p. 9.
(Continued)

*Primary Examiner* — Abdullahi Nur
(74) *Attorney, Agent, or Firm* — Sand, Sebolt & Wernow Co., LPA

(57) ABSTRACT

The invention relates to a device for analyzing biological objects comprising a Raman spectroscopy system for capturing at least one Raman spectrum. The device comprises an arresting apparatus, which is designed to at least temporarily arrest the biological objects. An electronic computing apparatus is designed to determine a reaction of a biological object arrested by the arresting apparatus to at least one substance in accordance with an evaluation of the at least one Raman spectrum.

25 Claims, 14 Drawing Sheets

(51) Int. Cl.
*G01N 21/03* (2006.01)
*G01N 33/50* (2006.01)
*G21K 1/00* (2006.01)
*G01N 21/64* (2006.01)
*G01N 21/01* (2006.01)

(52) U.S. Cl.
CPC ......... *G01N 33/5094* (2013.01); *G21K 1/003* (2013.01); *G01N 21/64* (2013.01); *G01N 2021/0193* (2013.01); *G01N 2021/0346* (2013.01); *G01N 2021/651* (2013.01)

(58) Field of Classification Search
CPC ............ G01N 21/84; G01N 1/00; G01N 1/40; G01N 33/483; G01J 3/44; G01J 1/42; A61B 6/00
See application file for complete search history.

(56) References Cited

U.S. PATENT DOCUMENTS

| | | | |
|---|---|---|---|
| 2010/0315629 A1* | 12/2010 | Knopp | G01J 3/02 356/301 |
| 2013/0171685 A1 | 7/2013 | Schuetze et al. | |
| 2014/0322729 A1 | 10/2014 | Fan et al. | |

OTHER PUBLICATIONS

Janice L. Panza et al: "Raman spectroscopy and Raman chemical imaging of apoptotic cells", Biomedical Photonics and Optoelectronic Imaging : Nov. 8-10, 2000, Beijing, China, vol. 6441, Feb. 8, 2007 (Feb. 8, 2007), p. 644108, XP055259734, Bellingham, Wash., US DOI: 10.1117/12.701219 ISBN: 978-1-62841-832-3 the whole document.

* cited by examiner

DEVICE AND METHOD FOR ANALYZING BIOLOGICAL OBJECTS WITH RAMAN SPECTROSCOPY

FIELD OF THE INVENTION

Examples of the invention relate to devices and methods for the investigation of biological objects. Examples of the invention relate in particular to devices and methods by means of which cells, cell clones, bacteria or other biological objects can be analyzed, for example in order to investigate and/or detect reactions of the cells to active substances, compatibility of cosmetics and other substances, toxicity of chemical substances or diseases such as sepsis or drug resistance. Such devices and methods can also optionally be configured to sort biological objects for further testing or to make personalized treatments possible.

BACKGROUND

Methods for analyzing biological objects, for example, methods for analyzing cells, cell clones, bacteria or other biological objects, continue to be used. Examples of applications in which it is desirable to analyze biological objects with respect to their properties or behavior include the determination of reactions to active substances, drug resistance, the detection of pathological states such as sepsis, and the determination of compatibility of active substances and chemicals.

For reasons of reproducibility and reliability, it can also be desirable to carry out measurements on a plurality of biological objects and/or to repeatedly measure the same biological object. For example, it can be desirable to detect reactions or resistance to a plurality of active substances or to observe reactions over a prolonged period. In such measurements on a plurality of biological objects and/or repetitions of measurements on the same object, temporal factors can be particularly significant. By means of measurements repeated over time, one can carry out serial measurement, also referred to in the art as monitoring.

SUMMARY

There is a need for devices and methods for investigating biological objects. In this context, there is a particular need for devices and methods that allow investigation of biological objects in a physiological environment such as a cell culture medium. These biological objects are of particular interest in a native or vital state that can be maintained beyond the time period of testing. In particular, there is a need for devices and methods that are suitable for measurement of a plurality of biological objects and/or repeated measurement of the same biological object, wherein by means of quantitative measurement values, findings can be obtained on the properties or behavior of the biological objects in an objective manner. Optionally, suitability for sorting the biological objects would be desirable.

According to examples of the invention, devices and methods are provided in which biological objects are analyzed by means of Roman spectra. An arresting unit is configured to at least temporarily arrest each of a plurality of biological objects. The term "arrest" as used herein refers to the non-destructive holding of a biological object in place. In this context, metabolic and/or cellular functions and/or interactions remain intact together with the environment of the biological object. Moreover, lysis, chemical fixation, destruction, or disintegration of the biological objects is prevented. In this manner, "arresting" of a biological object also allows analysis of biological objects according to the invention by means of Raman spectroscopy over a longer period of time. For example, arrested biological objects can be non-destructively analyzed for a few minutes, several hours, for example 4, 5, 6, 8, 10, 12, 15, 20, or 24 hours, 1, 2, 3, 4, 5, 6, or 7 days, or more than week, thus allowing long-term analysis or repeated analysis of biological objects, in certain embodiments also with different concentrations or different combinations of active substances as described herein. In particular embodiments, fixation of the biological objects can be carried out by chemical or biochemical interaction with a holding area. In these embodiments, the biological objects are held in such a way that they are in a moist state that allows exchange of molecules, substances and/or metabolites of the biological objects, for example living cells, with the environment. It is also provided that in particular embodiments, the fixation is reversed in order to maintain cells in a vital and/or viable state. In this context, an arresting unit according to the invention can be configured as a sample-receiving device that makes it possible to receive biological objects to be investigated, for example living cells or cell clusters, for a limited period such as the test period or a series of test periods, and to keep them in a form and position so as to allow active substance exposure and Raman spectroscopic analysis of the biological objects.

In certain embodiments, biological objects can be arrested within a fixed matrix, composed for example of a hydrogel or a polymer mesh. Bringing the substance into contact with such a matrix allows it to penetrate into the matrix and come into contact with the arrested biological objects, for example native cells. The effect of the substance on the biological object can then be temporally and spatially followed in a Raman spectroscopy system as described herein.

In further embodiments, biological objects can be present free in solution and be separated from one another by means of physical spatial boundaries. For example, such boundaries may be µ-vessels, laminar flows, or optically induced retaining forces such as optical tweezers that make it possible to hold the biological objects within a specified space. They also make it possible to clearly identify the biological objects after or during the analysis. This allows a biological object identified in this manner to be supplied for specific further analysis or cultivation, storage, etc.

In such embodiments, at least one part of these reaction spaces is advantageously open, for example on one side or two or more sides. Via this open area or these open areas, for example, a fluid stream can flow containing a substance to be tested that penetrates into the reaction space or spaces via diffusion. In this case, the fluid stream itself does not carry the biological objects out of the reaction spaces, because in microfluidics, a laminar flow prevails that is not capable of transporting objects outside of the stream. Preferred are substances to be tested that are transported with the fluid stream and exchanged between the fluid stream and the reaction space via diffusion. In further embodiments, this allows the provision of different substances, a plurality of substances at the same time, different concentrations of substances, gradients of substance concentrations, and/or the temporally controlled and/or periodic delivery of substances as described herein.

In order to arrest the respective biological object, it can be fixed on a spatial area, which for example is a cavity in a microstructure or a section of a coating on a carrier.

In a particular embodiment of the invention, a laminar flow is present in a microfluidic channel that arranges the biological objects such that respective individual objects flow or are transported successively at different times. In this configuration, the biological objects can be arranged as beads or chains of beads. The Raman spectroscopy system according to the invention is thus configured and can be used in order to individually acquire the correspondingly arranged biological objects, optionally position them by means of optical retaining forces, and arrest them during Raman measurement. This allows simultaneous analysis of the biological objects during the transport process.

The same biological object or different biological objects can be repeatedly engaged by a Raman spectroscopy system in order to acquire a plurality of Raman spectra that are assigned to the same biological object or different biological objects. In order to automate the process, an overview image of the biological objects arrested by an arresting unit can be acquired using an image acquisition device. The overview image can be automatically evaluated in order to generate control signals for an actuator that produces a relative movement between the arresting unit and the Raman spectroscopy system. In this case, the Raman spectroscopy system is a system that allows non-destructive analysis of biological objects. Such a system is based on arresting and analysis of biological objects that allows the investigated biological objects to survive, i.e. does not cause any lysis, disintegration, chemical decomposition, or similar destruction of the activity of the biological objects. In specific embodiments, therefore, it is even possible to reuse or recover the biological objects. In further particular embodiments, the Raman spectroscopy system according to the invention is a system that does not require any surface coating of a carrier material in order to obtain Raman spectra. In further particular embodiments, the Raman spectroscopy system according to the invention is an SERS-Raman spectroscopy system.

The respective Raman spectra can be acquired on the biological objects themselves and/or on material surrounding the biological objects. For example, one or a plurality of Raman spectra can be acquired on cells or cell clones. Alternatively or additionally, one or a plurality of Raman spectra can be acquired in a fluid that at least partially surrounds the cell or cell clone. In this manner, metabolites discharged from one or a plurality of cells can be detected. The reaction of biological objects to one or a plurality of substances can be determined by means of metabolites that are detected in an environment of the biological objects. The device according to the invention and methods for analyzing biological objects according to the invention are thus based not on detection of the substances used themselves, but on an analysis of the reaction of a biological object to these substances.

The devices and methods can carry out automatic sorting of biological objects in accordance with the Raman spectra acquired on the biological objects themselves and/or in accordance with the Raman spectra acquired on a fluid surrounding the biological objects. For the sorting of biological objects, fluid flows in a fluidic chip, optical radiation such as optical tweezers, electrical or magnetic fields, or other techniques can be used. The sorting of biological objects according to the present invention, which can be carried out automatically, can thus take place in accordance with the measured Raman spectra, and this makes it possible both to selectively remove and/or sort cells based on their reaction to a substance and to selectively remove and/or sort cells showing Roman spectra that are deviating, conspicuous, have previously been defined as interesting, etc.

The devices and methods according to the examples can be used for numerous applications. For example, the devices and methods can be used in order to detect resistance to active substances in order to identify effective personalized therapies so as to evaluate the compatibility of chemical substances and/or automatically detect sepsis or other pathological states by means of acquisition and evaluation of Raman spectra.

The devices and methods according to the present invention thus allow arresting and analysis of biological objects in three-dimensional space. This aspect, which is implemented in certain embodiments, makes it possible for example to acquire Raman spectra in cells or cell clones that are present in one cell layer or a plurality of cell layers. This allows Raman spectra to be obtained that provide accurate information on active substance reactions or resistance of biological objects in three-dimensional spaces of 1, 2, 3, 4, 5 or more cell layers. For example, such cell layers can have thicknesses of between 1 μm and 500 μm. In particular embodiments, cell layers can have a thickness of 1 μm, 2 μm, 3 μm, 4 μm, 5 μm, 10 μm, 15 μm, 20 μm, 30 μm, 40 μm, 50 μm, 100 μm, 150 μm, 200 μm, 250 μm, 300 μm, 350 μm, 400 μm, 450 μm or 500 μm. In this connection, as a rule, the thickness of the cell layers depends on the cell type and the type of sample to be investigated. In the case of individual cells, thicknesses or diameters in the range of 1-15 μm can therefore be present and analyzed. In the case of cell clusters, in particular small cell clusters or spheroids, which can also be analyzed by the system described herein, a layer thickness or diameter can be in the range of 50-300 μm. Also provided is the analysis of cell layers having a thickness lying between the above-mentioned values or smaller or larger than them. This also makes in situ analysis of multi-layer accumulations of biological objects possible.

A device for analyzing biological objects according to an example comprises a Raman spectroscopy system for acquiring at least one Raman spectrum. The device comprises an arresting unit that is configured to at least temporarily arrest the biological objects. The device comprises an electronic computing unit that is configured to determine a reaction of a biological object arrested by the arresting unit to at least one substance in accordance with an evaluation of the at least one Raman spectrum.

The device can be configured to measure a Raman spectrum either on a biological object or on a fluid covering or surrounding the biological object. The fluid can be a liquid.

The device can be configured to acquire a Raman spectrum before administration of the at least one substance and a further Raman spectrum after administration of the at least one substance. The computing unit can be configured to determine the reaction of the biological object to the at least one substance by means of a comparison of the Raman spectrum acquired before administration of the at least one substance and the Raman spectrum acquired after administration of the at least one substance.

The device can be configured to process a Raman spectrum assigned to a biological object using a further Raman spectrum that represents a Raman scattering on the arresting unit. For this purpose, an actuator can be activated in such a way that the further Raman spectrum is acquired at a location of the arresting unit that holds no biological object. The computing unit can carry out a background correction for all respective Raman spectra assigned to the biological objects, said background correction being in accordance with the further Raman spectrum that represents the Raman scattering on the arresting unit. For example, a difference spectrum can be determined in order to separate the Raman spectrum of a biological object or a metabolite from the Raman scattering on the arresting unit.

The computing unit can be configured to determine the reaction of the biological object to the at least one substance by means of a statistical evaluation of the Raman spectrum acquired before administration of the at least one substance and the Raman spectrum acquired after administration of the at least one substance. The statistical evaluation can comprise a main component analysis, a cluster analysis and/or a linear discriminant analysis (LDA).

The device can be configured to repeatedly engage the biological object arrested by the arresting unit in order to acquire the at least one Raman spectrum. The device can be configured to engage one and the same biological object to acquire one Raman spectrum before administration of the at least one substance and a further Raman spectrum after administration of the at least one substance, wherein between the two acquisitions, an actuator causes a relative movement between the arresting unit and the Raman spectroscopy system.

The device can comprise an actuator that is controllable by the electronic computing unit configured for producing a relative movement between the arresting unit and the Raman spectroscopy system. The actuator can be activated in such a way that the time required for a biological object to react to a substance before a further Raman spectrum is acquired can be used for acquisition of Raman spectra on other biological objects. For this purpose, the actuator can carry out acquisitions of a relative movement between the arresting unit and the Raman spectroscopy system in order to effectively utilize measuring times.

The electronic computing unit can be configured to control the actuator in accordance with distances between at least two biological objects arrested by the arresting unit.

The electronic computing unit can be configured to control the actuator such that a Raman spectrum assigned to a first biological object is acquired, while at the same time, a second biological object, which is held on the arresting unit at a distance from the first biological object, is exposed to the at least one substance.

The device can comprise an image acquisition device coupled to the electronic computing unit that is configured to acquire an image of the biological objects arrested by the arresting unit. The electronic computing unit can be configured to control the actuator in accordance with the acquired image.

The electronic computing unit can be configured to control the actuator such that sequential Raman spectra are acquired that are assigned to different biological objects. In a plurality of successive acquisition sequences, each of a plurality of biological objects can be engaged multiple times to acquire Raman spectra in order to determine the reaction to one or a plurality of substances over the course of time, i.e. in a time-dependent manner.

The image acquisition device can comprise an optical path that is separate from a lens of the Raman spectroscopy system. In this manner, rapid navigation using the overview image acquired by the image acquisition device can be combined with high local resolution by means of the Raman spectroscopy system.

The image acquisition device can comprise a plurality of lenses, all of which are different from the lens of the Raman spectroscopy system.

The device can be configured such that at least one lens of the optical system of the image acquisition device is also used for irradiation of excitation light and/or in order to acquire scattered light in the Raman spectroscopy.

The arresting unit can comprise holding areas at each of which at least one biological object is arrestable.

The device can be configured to produce a fluid stream that flows over, around, or through the plurality of holding areas. The device can comprise a pump or another device for producing a fluid stream that flows over the plurality of holding areas.

The device can be configured to move a biological object from the fluid stream to a holding area and/or from the holding area to the fluid stream.

The device can be configured to move the biological object in a direction transverse to a flow direction of the fluid stream in order to at least temporarily arrest the biological object and/or in order to detach the biological object from the arresting unit. The device can be configured to move the biological object in a direction perpendicular to a flow direction of the fluid stream in order to at least temporarily arrest the biological object and/or in order to detach the biological object from the arresting unit.

The device can be configured to reversibly move a biological object in a non-destructive manner from the fluid stream to a holding area of the arresting unit and back into the fluid stream.

The device can comprise a source of electromagnetic radiation that is configured to move a biological object from the fluid stream to a holding area and/or from the holding area to the fluid stream.

The source of electromagnetic radiation can comprise optical tweezers.

The respective holding areas can be dimensioned so that only exactly one biological object is arrestable at each holding area.

The arresting unit can comprise a plurality of recesses, each of which serves as a holding area for temporary arresting of a biological object.

Each of the plurality of recesses can be dimensioned such that in each case, only exactly one cell or exactly one bacterium can be accommodated in the corresponding recess.

The plurality of recesses can be dimensioned such that a plurality of biological objects, for example, a cell clone with a plurality of cells, can be contained therein. The dimensions of the plurality of recesses can be selected such that they limit the size of a cell clone contained therein.

The respective holding areas can be dimensioned so that only exactly one cell is arrestable at each holding area.

The respective holding areas can be dimensioned so that a plurality of biological objects is arrestable at each of the holding areas.

The respective holding areas can be dimensioned so that a plurality of cells is arrestable at each of the holding areas.

The arresting unit can comprise a microslide.

The arresting unit can comprise a microwell plate.

The device can comprise a supply unit for supplying the at least one substance to the biological objects.

The supply unit can be configured to supply a plurality of different substances to the biological objects.

The supply unit can comprise at least one reservoir for a substance in order to supply the substance to a biological object.

The supply unit can be configured to allow accumulation of isolated cells present in a large sample volume. This can take place, for example, by eliminating the cells that are not of interest in a preceding lysis step or using centrifugal or centripetal forces by means of corresponding configuration of fluidic channels. Alternatively or additionally, such accumulation can be carried out using osmotic forces by means of selective membrane diffusion.

The supply unit can comprise reservoirs for a plurality of different substances. The supply unit can be configured to supply a first substance to a first biological object and to supply a second substance to a second biological object held on the arresting unit at a distance from the first biological object, said second substance being different from the first.

The supply unit can be configured to supply the different substances to different biological objects in a temporally coordinated manner, for example simultaneously or with a time lag.

At least one substance can be an active substance. The substances can comprise a plurality of active substances that are different from one another. Examples of suitable active substances include biomolecules, biochemical substances, proteins, amino acids or the like.

Alternatively or additionally, the at least one substance can be a chemical the compatibility of which is to be tested. The substances can comprise a plurality of chemicals that are different from one another.

Alternatively or additionally, at least one substance can be a toxin the action of which is to be tested. The substances can comprise a plurality of toxins that are different from one another. A toxin can be a chemical, for example a small organic or inorganic molecule. A toxin can also be a biological molecule, for example a peptide or protein. Moreover, the substance can be a biologically active substance, for example a living organism, a cell, a bacterium, a virus, a bacteriophage, or parts or combinations thereof. Examples of bacteria include Gram-positive staphylococci, streptococci and enterococci, as well as Gram-negative *Escherichia, Klebsiella, Serratia* and *Pseudomonas*.

The electronic computing unit can be configured to determine the reaction to a plurality of substances in accordance with an evaluation of the at least one Raman spectrum and/or to follow the course of the reaction in a time-dependent manner in accordance with the evaluation of a plurality of Raman spectra.

For a plurality of biological objects, the computing unit can compare a first Raman spectrum before administration of a substance and a second Raman spectrum after administration of a substance by means of a statistical evaluation. The statistical evaluation carried out by the computing unit can comprise a main component analysis, a cluster analysis and/or a linear discriminant analysis (LDA).

The electronic computing unit can be configured to detect resistance to an active substance in accordance with an evaluation of the at least one Raman spectrum.

The electronic computing unit can be configured to detect, in accordance with the evaluation of a plurality of Raman spectra, to which of a plurality of active substances resistance is present.

The electronic computing unit can be configured to determine, in accordance with the evaluation of a plurality of Raman spectra, which chemicals are incompatible with an organism.

The electronic computing unit can be configured to determine, in accordance with the evaluation of a plurality of Raman spectra, what action toxins have on an organism.

The electronic computing unit can be configured to determine, in accordance with the evaluation of a plurality of Raman spectra, what action a biologically active substance has on an organism.

The electronic computing unit can be configured, in order to detect drug resistance, to compare a first Raman spectrum acquired before supplying the at least one substance with a second Raman spectrum acquired after administration of an active substance.

The at least one substance can comprise an active substance, a toxin, a biologically active substance and/or a chemical.

The device can be configured such that the at least one Raman spectrum acquired by Raman scattering on a biological object is evaluated by the electronic computing unit.

The device can be configured such that the at least one Raman spectrum evaluated by the electronic computing unit is acquired by Raman scattering on a material different from the biological object.

The device can be configured to determine in parallel the reactions of a plurality of biological objects to a substance or a plurality of substances.

A method for analyzing biological objects comprises arresting of a biological object by an arresting unit. The method comprises acquiring at least one Raman spectrum of the arrested biological object. The method comprises an evaluation of the at least one Raman spectrum in order to determine a reaction of a biological object to at least one substance.

The method can be carried out with the device according to an example.

In the method, a Raman spectrum can be acquired either on a biological object or on a fluid covering or surrounding the biological object. The fluid can be a liquid.

In the method, one Raman spectrum can be acquired before administration of the at least one substance and a further Raman spectrum can be acquired after administration of the at least one substance. A computing unit can determine the reaction of the biological object to the at least one substance by comparing the Raman spectrum acquired before administration of the at least one substance with the Raman spectrum acquired after administration of the at least one substance.

In the method, a Raman spectrum assigned to a biological object using a further Raman spectrum that represents a Raman scattering on the arresting unit can be processed. For this purpose, an actuator can be activated such that the further Raman spectrum is acquired at a location of the arresting unit that holds no biological object. A computing unit can carry out a background correction for all Raman spectra respectively that are assigned to biological objects, said background correction being in accordance with the further Raman spectrum that represents the Raman scattering on the arresting unit. For example, a difference spectrum can be determined in order to separate the Raman spectrum of a biological object or a metabolite from the Raman scattering on the arresting unit.

The reaction to the substance(s) can be determined in the method in that the reaction of the biological object to the at least one substance is determined by means of a statistical evaluation of the Raman spectrum acquired before administration of the at least one substance and the Raman spectrum acquired after administration of the at least one substance. The statistical evaluation can comprise a main component analysis, a cluster analysis and/or a linear discriminant analysis (LDA).

In the method, the biological object arrested by the arresting unit can be repeatedly engaged in order to acquire the at least one Raman spectrum. In the method, one and the same biological object can be engaged to acquire one Raman spectrum before administration of the at least one substance and a further Raman spectrum after administration of the at least one substance, wherein between the two acquisitions, an actuator causes a relative movement between the arresting unit and the Raman spectroscopy system.

In the method, a controllable actuator can be controlled in order to produce a relative movement between the arresting unit and the Raman spectroscopy system. The actuator can be activated in such a way that the time required for a biological object to react to a substance before a further Raman spectrum is acquired is used for acquisition of Raman spectra on other biological objects. For this purpose, the actuator can carry out acquisitions of a relative movement between the arresting unit and the Raman spectroscopy system in order to effectively utilize measuring times.

In the method, the actuator can be controlled in accordance with distances between at least two biological objects arrested by the arresting unit.

In the method, the actuator can be controlled such that a Raman spectrum assigned to a first biological object is acquired, while at the same time, a second biological object, which is held on the arresting unit at a distance from the first biological object, is exposed to the at least one substance.

In the method, it is possible with a single image acquisition device to acquire an image of the biological objects arrested by the arresting unit. The actuator can be controlled independently of the acquired image.

In the method, the actuator can be controlled such that sequential Raman spectra are acquired that are assigned to different biological objects. In a plurality of successive acquisition sequences, each of a plurality of biological objects can be engaged multiple times to acquire Raman spectra in order to determine the reaction to one or a plurality of substances over the course of time.

In the method, the image acquisition device can comprise an optical path that is separate from a lens of the Raman spectroscopy system. In this manner, rapid navigation using the overview image acquired by the image acquisition device can be combined with high local resolution by means of the Raman spectroscopy system.

The image acquisition device can comprise a plurality of lenses, all of which are different from the lens of the Raman spectroscopy system.

At least one lens of the optical system of the image acquisition device can also be used for irradiation of excitation light and/or in order to acquire scattered light in the Raman spectroscopy. The lens of the optical system can be a lens of a microscope through which the excitation beam is guided.

In the method, the arresting unit can comprise holding areas at each of which at least one biological object is arrestable.

The method can comprise the production of a fluid stream that flows over, around, or through the plurality of holding areas. The fluid stream that flows over the plurality of holding areas can be produced by means of a pump or another device for producing a fluid stream.

In the method, a biological object can be moved from the fluid stream to a holding area and/or from the holding area to the fluid stream.

In the method, the biological object can be moved in a direction transverse to a flow direction of the fluid stream in order to at least temporarily arrest the biological object and/or in order to detach the biological object from the arresting unit. In the method, the biological object can be moved in a direction perpendicular to a flow direction of the fluid stream in order to at least temporarily arrest the biological object and/or in order to detach the biological object from the arresting unit.

In the method, a biological object can be reversibly moved in a non-destructive manner from the fluid stream to a holding area of the arresting unit and back into the fluid stream.

In the method, a source of electromagnetic radiation can be controlled in order to move a biological object from the fluid stream to a holding area and/or from the holding area to the fluid stream.

The source of electromagnetic radiation can comprise optical tweezers.

In the method, the respective holding areas can be dimensioned such that only exactly one biological object is arrestable at each holding area.

In the method, the arresting unit can comprise a plurality of recesses, each of which serves as a holding area for temporary arresting of a biological object.

In the method, the plurality of recesses can respectively be dimensioned such that in each case, only exactly one cell or exactly one bacterium can be accommodated in the corresponding recess.

In the method, the plurality of recesses can be dimensioned such that a plurality of biological objects, for example, a cell clone with a plurality of cells, can be accommodated therein. The dimensions of the plurality of recesses can be selected such that they limit the size of a cell clone accommodated therein.

In the method, the respective holding areas can be dimensioned such that only exactly one cell is arrestable at each holding area.

In the method, the respective holding areas can be dimensioned such that a plurality of biological objects is arrestable at each of the holding areas.

In the method, the respective holding areas can be dimensioned such that a plurality of cells is arrestable at each of the holding areas.

In the method, the arresting unit can comprise a microslide.

In the method, the arresting unit can comprise a microwell plate.

In the method, a supply unit for supplying the at least one substance to the biological objects can be automatically controlled.

In the method, the supply unit can be configured to supply a plurality of different substances to the biological objects.

In the method, the supply unit can comprise at least one reservoir for a substance in order to supply the substance to a biological object.

In the method, the supply unit can comprise reservoirs for a plurality of different substances. The supply unit can be configured to supply a first substance to a first biological object and to supply a second substance to a second biological object held on the arresting unit at a distance from the first biological object, said second substance being different from the first substance.

In the method, the supply unit can be configured to supply the different substances to different biological objects in a temporally coordinated manner, for example simultaneously or with a time lag.

At least one substance can be an active substance. The substances can comprise a plurality of active substances that are different from one another.

Alternatively or additionally, at least one substance can be a stimulant or a differentiating agent that stimulates the cells to change. For example, at least one substance can be a stimulant or a differentiating agent that stimulates the cells to undergo a behavioral change. The substances can comprise a plurality of active substances that are different from one another.

Alternatively or additionally, at least one substance can be a chemical the compatibility of which is to be tested. The substances can comprise a plurality of chemicals that are different from one another.

Alternatively or additionally, at least one substance can be a toxin the action of which is to be tested. The substances can comprise a plurality of toxins that are different from one another. A toxin can be a chemical, for example a small organic or inorganic molecule. A toxin can also be a biological molecule, for example a peptide or protein. Moreover, the substance can be a biologically active substance, for example a living organism, a cell, a bacterium, a virus, a bacteriophage, or parts or combinations thereof. Examples of microbes include Gram-positive staphylococci, streptococci and enterococci, as well as Gram-negative *Escherichia, Klebsiella, Serratia* and *Pseudomonas*.

In the method, one or a plurality of reservoirs can be provided in which selected sorted cells can be transported and deposited. The selected cells can be removed from this reservoir or reservoirs for further tests.

The electronic computing unit can be configured to determine the reaction to a plurality of substances in accordance with an evaluation of the at least one Raman spectrum and/or to follow the course of the reaction in a time-dependent manner in accordance with the evaluation of a plurality of Raman spectra.

In the method, for a plurality of biological objects, a first Raman spectrum before administration of a substance and a second Raman spectrum after administration of a substance can be compared in each case by means of a statistical evaluation. A statistical evaluation carried out by a computing unit can comprise a main component analysis, a cluster analysis and/or a linear discriminant analysis (LDA).

In the method, the electronic computing unit can recognize an active substance reaction in accordance with the evaluation of the at least one Raman spectrum.

In the method, the electronic computing unit can recognize drug resistance in accordance with the evaluation of the at least one Raman spectrum.

In the method, in accordance with the evaluation of a plurality of Raman spectra, the electronic computing unit can determine to which of a plurality of active substances resistance is present.

In the method, in accordance with the evaluation of a plurality of Raman spectra, the electronic computing unit can determine which chemicals are incompatible with an organism.

In the method, in accordance with the evaluation of a plurality of Raman spectra, the electronic computing unit can determine the action a toxin or a plurality of toxins has on an organism.

In the method, in accordance with the evaluation of a plurality of Raman spectra, the electronic computing unit can determine the action a biologically active substance or a plurality of active substances has on an organism.

In the method, in order to detect the drug resistance, the electronic computing unit can compare a first Raman spectrum acquired before supplying the at least one substance with a second Raman spectrum acquired after administration of an active substance.

In the method, the at least one substance can comprise an active substance, a biological active substance, a toxin and/or a chemical.

In the method, the at least one Raman spectrum evaluated by the electronic computing unit can be acquired by Raman scattering on a biological object.

In the method, the at least one Raman spectrum evaluated by the electronic computing unit can be acquired by Raman scattering on a material different from the biological object, for example, by Raman scattering on a fluid that covers the biological object.

In the method, the reaction of a plurality of biological objects to a substance or a plurality of substances can be determined in parallel.

In the devices and methods, the biological objects can be fixed. For fixation, the biological objects can be temporarily arrested in a 3D matrix. The biological objects can adherently grow onto a surface. A 3D matrix according to the invention can contain one or a plurality of layers of biological objects, for example cells. In certain embodiments, a 3D matrix can contain 2, 3, 4, 5, 6, 7 or more layers of biological objects, for example cells. The correspondingly positioned biological objects, for example cells, can grow in the 3D structure, for example undergoing cell division processes, and/or can interact with the environment, for example growing solidly into surface structures.

With the devices and methods according to the examples, the respective reactions of biological objects to one or a plurality of different substances can be followed in time-dependent fashion. In particular, biological objects can be analyzed in a non-destructive manner over a prolonged period of time of several hours, days, or weeks, for example in the form of a periodically repeated analysis, an analysis after multiple administration of substances, escalating administration of substances, administration of different substances in succession, etc. Data on the time-dependent course and kinetics of a reaction of the biological objects to the substances can be obtained by evaluation of a plurality of Raman spectra.

The devices and methods according to the examples allow rapid and marker-free testing of biological objects with respect to their reaction to substances such as active substances, toxins or chemicals. Such analysis methods can be used for example for detection of drug resistance, determination of chemical compatibility, automatic identification of effective personalized treatments, automatic mechanical disease detection, detection of sepsis, or in other areas. Moreover, the possibility of sorting biological objects according to the invention, as described herein, allows spatial separation of biological objects with specific patterns of reaction to administration of a substance, for example in a microfluid system as described herein. This allows assignment of biological objects to the detected analysis values. It is particularly advantageous in this context that the integrity and vitality of the biological objects, for example cells, which have been subjected to non-destructive analysis, are retained. In this manner, in particular embodiments, biological objects, for example cells, can be identified, sorted, and then supplied for further cultivation or expansion, or for further analysis.

BRIEF DESCRIPTION OF THE FIGURES

In the following, the invention is further explained with reference to the drawing by means of preferred examples.

DESCRIPTION OF EXAMPLES

The examples are described with reference to the figures, in which similar reference numbers indicate similar features. The features of the various embodiments described can be combined with one another, provided that this is not expressly excluded in the following description.

Devices and methods according to the examples can be used for investigating biological objects that are at least temporarily arrested by an arresting unit. In particular, devices and methods according to the examples can be used in order to detect and automatically evaluate a reaction of such biological objects to substances such as, for example, active substances, toxins or chemicals.

For example, the devices and methods according to the examples can be used for observation of cell differentiation, detection of drug resistance, automatic or computer-aided development of personalized treatments, computer-aided detection of pathological states, or for other purposes.

In devices and methods according to the examples, at least one Raman spectrum of a biological object is acquired. For example, the biological object can comprise a cell, a cell clone, a bacterium or another biological object. At least one Raman spectrum before administration of a substance and at least one further Raman spectrum during or after administration of the respective substance can be acquired on each of a plurality of biological objects respectively. By means of a statistical evaluation of one or a plurality of Raman spectra, it can be determined how the biological object reacts to the corresponding substance.

Different biological objects for which assigned Raman spectra are acquired can be exposed to different substances in order to determine the respective reaction to the corresponding substance. In this context, the reaction of a plurality of biological objects to a plurality of different substances can be monitored in parallel by Raman spectroscopy.

Figure 1:
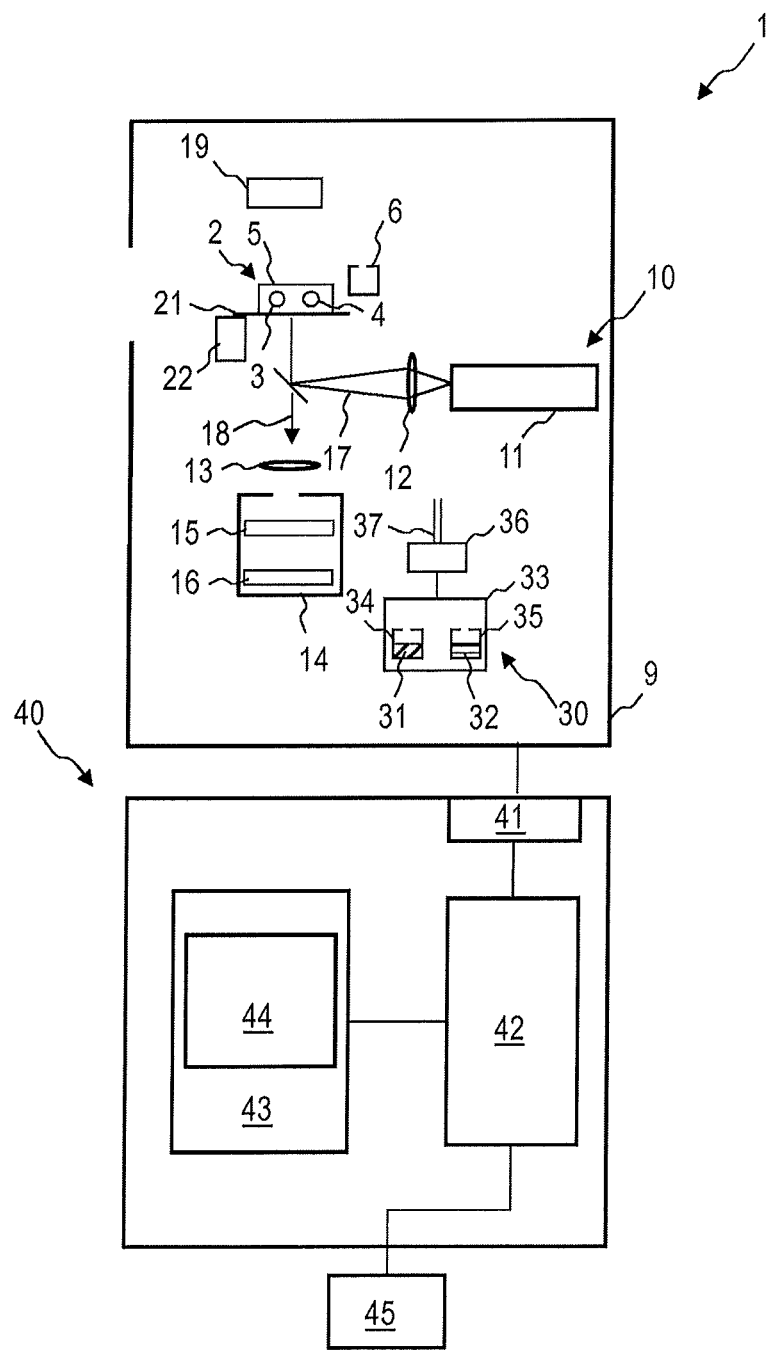
FIG. 1 shows a schematic view of a device according to an example.

FIG. 1 is a schematic view of a device 1 according to an example. The device 1 is configured to investigate biological objects 3, 4 of a sample 2 by Raman spectroscopy. During a measurement, the biological objects 3, 4 are at least temporarily arrested by an arresting unit 5. The term "arresting" as used here is generally understood to mean that the biological object is localized in a position. The biological object 3, 4 can, but does not have to, be immobilized. For example, the arresting can take place in specially coated areas of a slide. The arresting can be carried out by means of a gel-like matrix. Localization can take place for example in a recess of a microslide or a microwell plate that is slightly larger than the biological object 3, 4.

The device 1 can be configured to determine and automatically evaluate the reaction of one or a plurality of biological objects 3, 4, which are arrested by the arresting unit 5, to a substance or a plurality of different substances. The device 1 can comprise a supply unit 30 that is configured to supply one or a plurality of substances to one or a plurality of the biological objects 3, 4.

The device 1 comprises a Raman spectroscopy system 10 and a computing unit 40. The Raman spectroscopy system 10 is configured to acquire a Raman spectrum of a biological object or a plurality of biological objects 3, 4 that are arrested by the arresting unit 5. Each of the biological objects 3, 4 can be selected from a cell, a cell clone, a bacterium, and other biological objects.

The device 1 can optionally comprise a microscopy system for locating and/or observing microscopically small objects. Optionally, the device 1 can comprise a fluorescence unit, for example in order to excite autofluorescence of biological objects.

The Raman spectroscopy system 10 comprises a light source 11. The light source 11 can be a laser. The laser can have a cell-protecting laser wavelength. The laser wavelength can be 785 nm. The light source 11 is configured to emit an excitation beam 17. Such a Raman spectrometer 14 receives scattered light 18 at one or a plurality of the biological objects 3, 4 by Stokes processes and/or anti-Stokes processes. The Raman spectrometer 14 can comprise a diffractive element 15 and an image sensor 16 in order to acquire the Raman spectrum of a biological object 3, 4. In a manner known per se, the Raman spectroscopy system 10 can comprise further elements, for example focussing optical elements 12, 13, which can be configured as lenses and/or diaphragms.

The light source 11 can emit the excitation beam with a wavelength in the near infrared region. The light source 11 can emit the excitation beam with a wavelength that allows investigation of native cells by means of Raman spectroscopy.

The excitation beam 17 can be focused through a lens in such a way that an electromagnetic gradient is generated, by means of which biological objects can be drawn into the laser focus and held there. This can take place simultaneously with spectral acquisition, i.e. the objects are arrested in the laser focus by the Raman scattering. However, the optical retaining forces can also be used independently of the acquisition of Raman spectra, for example in order to transport the biological objects from one place to another.

The device 1 comprises a computing unit 40. The computing unit 40 can be a computer or comprise a computer. The computing unit 40 is coupled to the Raman spectroscopy system 10. The computing unit 40 can control the acquisition of the Raman spectrum by the Raman spectroscopy system 10.

The computing unit 40 can control the light source 11 such that it can be used once for acquisition of Raman spectra and, and in this process, the biological objects are simultaneously held in the laser focus. However, the light source 11 can also be activated such that it can hold and/or transport biological objects independently of the acquisition of a Raman spectrum.

The computing unit 40 can control the Raman spectroscopy system 10 such that Raman spectra are acquired in a spatially resolved manner on the biological objects 3, 4 arrested by the arresting unit 5. Different biological objects 3, 4 can be subjected to Raman spectroscopy sequentially in time, for example in order to determine their reaction to a substance. The activation by means of which the different objects are subjected to Raman spectroscopy sequentially in time can take place automatically.

The computing unit 40 comprises an interface 41 for receiving data from the image sensor 16 of the Raman spectroscopy system 10. The computing unit 40 comprises an integrated semiconductor circuit 42 that can comprise a processor and is configured to evaluate the acquired Raman spectrum. The integrated semiconductor circuit 42 is configured to evaluate the at least one Raman spectrum. For example, the integrated semiconductor circuit 42 can subject each of a plurality of acquired Raman spectra to one statistical analysis during or after exposure of the biological object to a substance. The statistical analyses can comprise a main component analysis, a cluster analysis and/or a linear discriminant analysis (LDA).

As described in further detail with reference to FIGS. 2 through 23, the integrated semiconductor circuit 42 can be configured to detect the presence or absence of specified Raman peaks or determine the spectral weight of Raman peaks that are associated with specified cell reactions. For example, the integrated semiconductor circuit 42 can be configured to quantitatively determine by evaluation of the at least one Raman spectrum whether cells, cell clones, bacteria, microbes or other biological objects show fundamental changes as a reaction to a substance, for example conversion to apoptosis, necrosis, or another functional state.

The integrated semiconductor circuit 42 can be configured to evaluate for one or a plurality of biological objects, in a time-dependent manner in each case, the reaction to the respective substance supplied to this biological object. In this manner, the reaction of a plurality of biological objects can be monitored in parallel and in time-dependent fashion either partially or fully automatically.

The integrated semiconductor circuit 42 can detect different cell types, for example different blood cells, by means of the position of Raman peaks, the peak height, the steepness of the flanks, and the characteristic distribution of the peaks (peak pattern) for the corresponding cell type. Data on the position and/or the spectral weight of different Raman peaks for the different cell types can be stored in a nonvolatile manner in a storage element of the device 1. Alternatively or additionally, the data on the position and/or the spectral weight of different Raman peaks for the different cell types, different bacteria, different microbes or other biological objects can be determined by the device 1 by methods of supervised learning or other machine learning methods.

The integrated semiconductor circuit 42 can process acquired Raman spectra in different ways. For example, statistical methods, for example a main component analysis, cluster analysis methods, or LDA methods can be used. Additionally or alternatively, Raman spectra can be compared with reference data in order to determine which cell types are present and the reactions of the cell types to different substances.

The computing unit 40 can comprise a storage element 43 in which the reference data 44 are deposited that can be used by the integrated semiconductor circuit 42 in evaluating the Raman spectrum.

The computing unit 40 can comprise an optical and/or acoustic output unit 45 via which data are output in accordance with the analysis of the at least one Raman spectrum. The device 1 can be configured to output data via the optical and/or acoustic output unit 45 that indicate drug resistance to one or a plurality of active substances, compatibility of one or a plurality of chemicals, and/or the action of one or a plurality of toxic substances.

The device 1 can comprise an image acquisition device 19. The image acquisition device 19 can be configured to acquire an image of the biological objects 3, 4 that are arrested by the arresting unit 5. The image acquisition device 19 can be coupled to the integrated semiconductor circuit 42. The integrated semiconductor circuit 42 can recognize the biological objects 3,4 by means of automatic object recognition in the acquired image.

The image acquisition device 19 can be configured such that its imaging optical system is separate from a lens of the Raman spectroscopy system 10. The image acquisition device 19 can be configured such that the optical path from the arresting unit 5 to an image sensor of the image acquisition device 19 does not pass through any optical components of the lens of the Raman spectroscopy system 10. Alternatively, the image acquisition device 19 can be configured such that the optical path from the arresting unit 5 to the image sensor of the image acquisition device 19 passes through at least one optical component of the lens of the Raman spectroscopy system 10.

The integrated semiconductor circuit 42 can activate an actuator 22 in accordance with the image acquired by the image acquisition device 19 in order to sequentially position different biological objects 3, 4 held by the arresting unit 5 for measurement by the Raman spectroscopy system. The integrated semiconductor circuit 42 can activate the actuator 22 in accordance with the relative position between two biological objects in order to sequentially position different biological objects for Raman scattering.

The actuator 22 can be configured to produce a relative movement between the arresting unit 5 and the Raman spectroscopy system 10. The actuator 22 can comprise a motor or another drive, such as a piezoelectric drive, in order to bring about the movement. The actuator 22 can be configured to produce the relative movement in two and preferably three spatial directions that are orthogonal to one another.

The actuator 22 can be configured to move a carrier 21, to which the arresting unit 5 is attached, relative to the Raman spectroscopy system 10. The actuator 22 can alternatively or additionally be configured to move at least one optical component of the Raman spectroscopy system 10 relative to the carrier 21. The carrier 21 can be a microscope stage.

The device 1 comprises a supply unit 30 for supplying at least one substance. The supply unit 30 can be configured to supply different biological objects 3, 4 to a plurality of different substances. The supply unit 30 can comprise a reservoir 34 for a substance 31. The substance 31 can comprise an active substance, a toxin, a chemical or another substance: the substance 31 can be present in solution. A conveying unit 36 can be configured to supply the substance 31 from the reservoir 34 to the arresting unit 5. The conveying unit 36 can comprise one pump or a plurality of pumps in order to convey different substances independently of one another. The conveying unit 30 can convey the substance 31 via a line 37 to a supply element that supplies the substance 31 to a biological object 3. The conveying unit 30 can be configured to selectively supply the substance 31 only to exactly one biological object or only one group of biological objects, so that the other biological objects are not exposed to the substance 31.

The supply unit 30 can comprise a further reservoir 35 for a further substance 32. The further substance 32 can be different from the substance 31 or the same as the substance 31. The further substance 32 can comprise an active substance, a toxin, a chemical or another substance: the further substance 321 can be present in solution. The conveying unit 36 can be configured to convey the further substance 32 from the further reservoir 35 to the arresting unit 5. The conveying unit 36 can be configured to adjust a volume flow of the further substance 32 independently of a volume flow of the substance 31 to the arresting unit 5. The conveying unit 30 can convey the further substance 32 via the line 37 or a different line therefrom to a supply element, which supplies the further substance 321 to a biological object 4. The conveying unit 30 can be configured to selectively supply the further substance 32 only to exactly one biological object or only one group of biological objects so that the other biological objects are not exposed to the further substance 32.

The line 37 can comprise a plurality of different lumina. The line 37 can be a multiple lumen line in which the various lumina are integrated into a tube in order to convey various substances 31, 34 via the same tube to the same or different biological objects 3, 4.

Instead of the line 37 or in addition to the line 37, a channel can be used in which the substances are transported. A laminar flow in the channel can transport the substances.

Although the Raman spectroscopy system 10 and the supply unit 30 in FIG. 1 are shown schematically as a structurally integrated unit, at least one part of the supply unit 30 can also be provided separately from a housing of the Raman spectroscopy system 10. For example, the reservoir 34 and/or the further reservoir 35, which are configured in a storage receptacle 33, can be provided separately from the housing of the Raman spectroscopy system 10.

The device 1 can comprise a collection area 6 in which objects that have been transported from the microwells of a microfluid chip by means of optical tweezers or other devices, and for example brought into a fluid channel or fluid stream, can be collected.

It can be possible to insert the reservoir 34 and/or the further reservoir 35 into the storage receptacle 33 and remove it/them from the storage receptacle 33 in a reversibly and non-destructively detachable manner.

Although the computing unit 40 and the Raman spectroscopy system 10 are shown schematically in FIG. 1 as separate units, the functions of the computing unit 40 can also be integrated into a housing of the Raman spectroscopy system 10. The Raman spectroscopy system 10 and the computing unit 40 can be configured as mobile, in particular portable units.

In methods according to the examples, the device 1 can be used in a number of different ways, and in particular with a number of different samples 2.

The arresting unit 5 can be a microstructure for the arrangement of biological objects, for example, cells and/or bacteria. Alternatively or additionally, the arresting unit 5 can bring about the arresting of biological objects, for example, cells and/or bacteria, in the interstices of a gel or a matrix.

The image pickup unit 19 can acquire a wide-area overview image, which is automatically evaluated in order to detect whether biological objects, for example, cells and/or bacteria, are arrested on the arresting unit 5.

The computing unit 40 can for example evaluate contrast data, dark field data, fluorescence and/or autofluorescence in order to determine the positions of biological objects.

The microstructure allows rapid automatic scanning of different biological objects. So-called microwells, i.e. recesses, with cells or other biological objects are saved. Raman spectra are acquired. As the biological objects are held in the microwells, for example by gravity, adhesion, or a meshwork, they can be automatically engaged and measured after administration of the active substance and at specified times.

The device 1 can comprise a spectral database. The computing unit 40 can automatically sort the acquired spectra according to the locations, for example the microwells, in which biological objects are contained. A kinetic course of the reaction of biological objects to one or a plurality of different substances can be determined. As will be described in further detail below, in order to determine the kinetic course of the reaction, a statistical evaluation of the Raman spectra can be carried out, for example by means of a main component analysis, a cluster analysis and/or an LDA.

The computing unit 40 can be configured to determine a species of the biological object, for example a cell type. For this purpose, the computing unit 40 can carry out matching with previously deposited characteristic spectra. The matching can also be carried out by statistical evaluation of the Raman spectra, for example, by means of a main component analysis, a cluster analysis and/or an LDA.

The device 1 can be configured for parallelization of the analysis of biological objects and/or their reaction to active substances, toxins, chemicals or other substances. For example, the device 1 can use the times at which an active substance is supplied to a biological object in order to acquire, and also optionally evaluate, a Raman spectrum of a further biological object that is not covered by a supply element.

An arresting unit 5 configured as a micromatrix can be used for the multiplexed analysis of cells, cell clusters or cell clones by means of Raman spectroscopy. In this case, the size of the microwells determines whether only one cell, cell clone or cell cluster that grows via reproduction of an individual cell is investigated by Raman spectroscopy.

In order to allow analysis of smaller biological objects, such as bacteria for example, a hydrogel or a similar matrix can be used as an arresting unit 5 to arrest said objects.

The device 1 can be configured to automatically compensate for background signals of the arresting unit 5. For this purpose, in addition to an acquisition of a Raman spectrum that is assigned to a biological object, the actuator 22 can be activated in such a way that the Raman spectrum of the arresting unit 5 is acquired at a position at which no biological object is present. By means of difference spectrum formation, in which for example a weighted difference of a Raman spectrum of a biological object and the Raman spectrum of the arresting unit 5 is determined, background-corrected Roman spectra can initially be obtained, which are then further analyzed using statistical analysis methods such as a cluster analysis, a main component analysis and/or an LDA in order to determine the kinetics of a reaction to a substance.

The device 1 can optionally be configured to sort biological objects. For this purpose, a microfluidic system can be used. The biological objects can be sorted in accordance with their reaction to one or a plurality of substances 31, 32.

For example, use of the device 1 for the detection of pathogenic microbes and evaluation of effective antibiotics is described in the following. The device 1 can be used both for the identification of bacterial pathogens in the bloodstream (bacteremia) and for the evaluation of the efficacy of antibiotics or other active substances. While the example described is the detection of pathogenic microbes and the determination of the reaction to active substances, other types of cells can also be investigated in order to determine the reaction of cells to active substances.

In order to identify bacterial pathogens in the bloodstream, the computing unit 40 can compare acquired Raman spectra with data for Raman spectra acquired for the following genera: Gram-positive staphylococci, streptococci and enterococci and Gram-negative *Escherichia, Klebsiella, Serratia* and *Pseudomonas*.

The device 1 allows the combination of rapid bacterial detection and determination of resistance. The device 1 allows the patient-specific determination of an optimally effective antibiotic in an automatic or computer-aided procedure. The length of the stay in the hospital for treatment could be sharply decreased, and costs could thus also be correspondingly reduced/saved. In addition, the probability of developing resistance would decrease in the long term.

For this purpose, in a first step, Raman spectra of living pure cultures of relevant pathogens of a bacterial sepsis can be measured, and these can be stored as Raman databases in the computing unit 40 or in a separate storage unit. In this case, both the bacteria themselves and their residues can be investigated by Raman spectroscopy.

Alternatively or additionally, blood samples from healthy persons can be measured and compared with those of the infected patients.

For subsequent identification of bacterial pathogens, samples of the blood plasma and the colonies from the blood cultures can be measured with the Raman spectroscopy system 10. The data obtained can be matched with the spectra of the databases in order to find typical detection patterns for the individual pathogens.

The arresting unit can be configured such that it eliminates the blood cells and accumulates the microbes at a predefined location for acquisition of the Raman spectra. For this purpose, the arresting unit can comprise a curved fluid channel and/or a membrane.

The device 1 can additionally allow resistance testing for identification of the microbes. For determination of resistance and in order to find suitable active substances, the pathogens are examined alive by the device 1. Different active substances 31, 32 can be supplied, wherein during or after supplying the active substances, respective Raman spectra of the biological objects are acquired in order to determine which active substance or which active substance combination they react to and/or to which substance or which active substances 31, 32 drug resistance is present.

The samples 2 and arresting units 5 used can show various configurations. For example, starting from a blood sample or a blood smear, the plasma can be separated from the serum and the cellular components by lysis of the cells and/or centrifugation or by means of a membrane. A pellet with the bacteria, remaining as sediment after centrifugation for example, or the corresponding layer after density gradient centrifugation can be applied to a slide, for example by pipetting. The arresting unit can also concentrate the bacteria via osmotic methods. The slide can be coated with a layer of a fine-meshed matrix, a so-called "scaffold." The matrix can comprise a hydrogel, collagen or agar. Optionally, the entire slide can be centrifuged so that the bacteria migrate into the layer. Alternatively, the bacteria can be mixed with the hydrogel, collagen, or agar and plated in the mixture so that the bacteria are arrested in the meshwork in the crosslinking process.

In this manner, the mobile microbes can be arrested in the pores of the matrix or the scaffold, so that they cannot swim away. The matrix as an arresting unit can store liquid, so that the bacteria can live and multiply therein. The device 1 can be configured to transport nutrients or active substances to the bacteria in the microincubator space. For example, the arresting unit can have an engraved surface in order to better locate the microbes microscopically or to relocate them after transfer into/from the incubator.

Optionally, the microbes can again be concentrated. For this purpose, the bacteria can be pressed through a fine-meshed matrix, for example hydrogel or collagen, which allows the liquid but not the microbes to pass through. In order to support its fragile consistency, the matrix can be applied to a lattice, for example an open-pore carrier with a lattice structure. At the same time, the lattice serves as a pattern to facilitate locating the microbes under a microscope on an image acquired with the image pickup unit 19. The carrier can be configured such that it can be transferred to a culturing dish with a glass bottom and measured by the Raman spectroscopy system 10.

For concentration, for example, a dual-tier sterile filtration unit can be used. Such a unit can comprise a plurality of segments in which filters with different pore sizes can be used. Osmosis can also be used for concentration.

After centrifugation for concentration purposes, the pellet or bands in question can be subjected to density gradient centrifugation with the bacteria mixed with a hydrogel, agar or a similar matrix and can be injected into microchannels or microwells for a cell culture. The individual microstructures can have a height of 100 µm to 3 mm. The individual microstructures can have a height of 50 µm to 3 mm.

During a crosslinking process, the microchannel slide can be centrifuged so that the bacteria, with the still liquid hydrogel or agar, can be deposited on the bottom or in the microwells.

The hydrogel or agar allows growth of the microbes in the microwells. On the one hand, the microbes can be measured and detected. At the same time, their growth can be observed. Active substances such as antibiotics can be injected into the different channels, and the reaction of microbes thereto can be measured by Raman spectroscopy.

After concentration, the microbes can lie on or at least immediately beneath the surface of the arresting unit 5. The structures of the arresting unit 5 limit the motility of the bacteria. The microbes can be automatically located by means of autofluorescence, for example, using an ultraviolet (UV) light, by evaluating the image acquired by the image pickup unit 19. Alternatively, the microbes can also be identified by a user and their positions can be plotted via a user interface. Alternatively or additionally, the microbes can be automatically detected and labeled using image analysis software. The meshwork of the matrix can be configured such that the bacteria cannot simply escape from the interstices and can therefore be more easily held and measured with a laser, for example by means of an optical trap. At the same time, the matrix can be configured such that nutrients can diffuse in the matrix in order to allow the growth of the bacteria to be followed and the action of antibiotics or other active substances 31, 32 to be tested.

In order to automate the analysis, the microwells of the arresting unit can automatically be optically scanned and checked for the presence of biological objects. Raman spectra can be measured using an optical trap effect, as even in fine-mesh matrices a certain residual freedom of movement of the microbes persists, so that they can be held by an optical trap during the Raman spectroscopy.

The Raman excitation during Raman spectroscopy can thus, in specific embodiments, simultaneously generate an optical trap. In such embodiments it is even possible to generate a Raman excitation as an electromagnetic gradient field by means of coupling technology, for example using free beam guidance, not using a fiber guide, and focussing the laser, for example an individual laser, through a lens. This leads to a trapping effect, i.e. an optical trap is generated. The present invention utilizes these possibilities in order to analyze and arrest biological objects.

In a further embodiment, the device according to the invention can be configured such that it comprises more than one laser, for example two lasers. Typically, the device comprises at least one laser for the Raman excitation and at least one second laser, which generates an optical trap for the biological object.

As will be described in further detail below, Raman spectra can be measured before the administration of active substances and after or during administration of active substances. It is possible, but not absolutely necessary, to repeat the measurements on the identical biological objects 3, 4. The measurements can be repeated in a time series in order to determine in time-independent fashion the reaction to one or a plurality of active substances 31, 32. The acquired Raman spectra can be further analyzed in various ways in order to determine reaction kinetics, as further described with reference to FIGS. 1 through 23. In particular, fully and partially automated data analysis can be carried out, by means of which the computing unit 40 determines the active substances 31, 32 to which drug resistance is present and/or which active substances 31, 32 allow promising therapy for the respective patients.

By evaluation of the Raman spectra, the reaction of biological objects 3, 4 to the active substances 31, 32 can be directly detected. By means of the device 1, suitable antibiotics or other active substances can automatically be detected. If a bacterial mixture is present, the respective microbes or colonies can be measured after specified periods.

For example, the devices and methods according to the examples allow the automatic determination of personalized treatments for pathologic states such as a sepsis without being limited hereto. Based on a live blood smear or directly from a drop of blood, it can be determined which microbes are present and/or which active substances allow successful treatment. The drops of blood can for example be placed in a special fluidic chip configured to eliminate the blood cells and concentrate the microbes, which can then be investigated by Raman scattering.

By means of the devices and methods according to the examples, biological objects such as cells, cell clusters, cell clones, microbes, for example bacteria, or other biological objects can be investigated without using markers. The cells can be investigated alive and non-destructively. Devices and methods can be implemented so that no pretreatment with marker molecules is required. The reaction to substances such as active substances, toxins, chemicals or other substances can be determined in a marker-free manner without requiring physical contact between a measurement unit and the biological objects for this purpose. The measurement throughput can be increased compared to other measuring techniques.

Further features of devices and methods according to the examples are described in further detail with reference to FIGS. 2 through 23.

Figure 2:
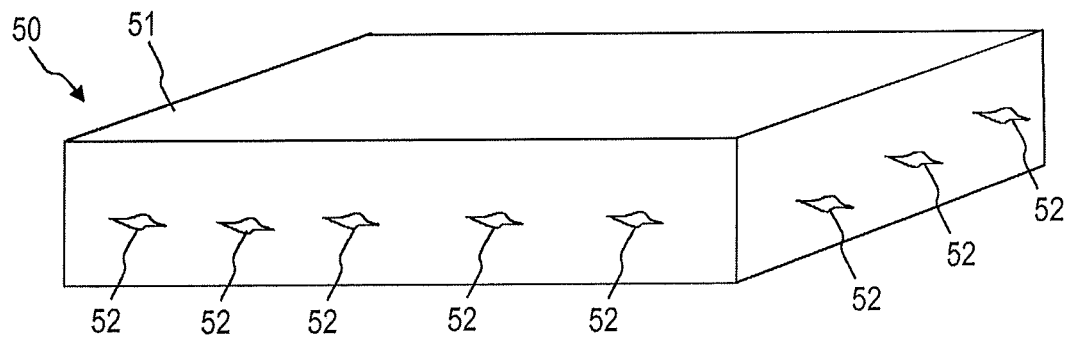
FIG. 2 shows biological objects on an arresting unit of a device according to an example.

FIG. 2 shows a schematic view of a sample 50 that comprises an arresting unit 51. The arresting unit 51 can be used in the device 1. The arresting unit 51 can comprise a hydrogel, a collagen or another material. The arresting unit 51 can comprise cavities for accommodating biological objects 52. The cavities can be configured such that they are permeable to nutrients for the biological objects 52.

In use of the arresting unit 51, the device 1 can automatically determine the positions of the biological objects 52 in the arresting unit 51. For this purpose, the computing unit 40 can automatically evaluate the image acquired by the image acquisition device 19. For example, autofluorescence of the biological objects 52 can be used for positional detection. For this purpose, the device 1 can comprise a light source for exciting the autofluorescence.

The device 1 can control the excitation laser and the image sensor of the Raman spectroscopy system 10 and the actuator 22 in accordance with the acquired positions of the biological objects 52 in order to selectively acquire Raman spectra on different biological objects 52. Substances such as active substances, toxins, chemicals or other substances can be conveyed from the supply unit 30 to the arresting unit 51 in order to observe the reaction of the biological objects 52 to the substance(s).

The hydrogel, collagen or another matrix, in the interstices of which biological objects 52 are held, can additionally be placed in a microwell plate or another microslide, as will be described in further detail with reference to FIGS. 3 through 10.

Figure 3:
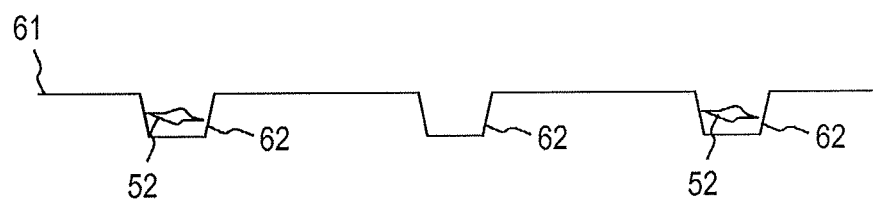
FIG. 3 shows biological objects on an arresting unit of a device according to an example.

FIG. 3 shows a schematic view of a sample that comprises an arresting unit 61. The arresting unit 61 can be used in the device 1. The arresting unit 61 can be configured as a microwell plate or another device comprising a plurality of receptacles 62 for accommodating biological objects. Each of the receptacles 62 can be configured as recesses, for example as microwells. However, the receptacles 62 can also be areas with a coating having increased cell adhesiveness to which the cells can adhere. For example, the coating can be a hydrophilic coating.

The receptacles 62 can have a depth and/or lateral dimensions that are adapted to the dimensions of the biological objects to be measured. For example, the receptacles 62 can be dimensioned such that only one cell each of the desired cell type can be accommodated in the receptacle 62. The receptacles 62 can also be dimensioned in order to accommodate cell clones or cell clusters that comprise a plurality of cells.

In further embodiments, the receptacles 62 can be configured as microwells and adapted in such a manner that when active substances such as toxins are flushed in, biological objects such as cells or cell clones located in the microwells cannot be flushed out of said microwells.

A preferred configuration of the microwells provides that they have a depth corresponding at least to their diameter.

In use of the arresting unit 61, the device 1 can automatically determine the positions of the receptacles 62. For this purpose, the computing unit 40 can automatically evaluate the image acquired by the image acquisition device 19 in order to detect the position and type of the receptacles 62 of the arresting unit 61.

The device 1 can further be configured to automatically determine in which of the receptacles 62 biological objects 52 are positioned. For this purpose, transmission or darkfield illumination can be used. However, for example, the autofluorescence of the biological objects 52 can also be used. Additionally, the objects can be charged with fluorescent molecules so that fluorescence-labeled cells can be selectively identified. For this purpose, the device 1 can comprise a light source for excitation of the autofluorescence or fluorescence. The positions of the receptacles 62, in each of which a biological object is positioned, can be stored in a storage element of the computing unit 40. For optimal utilization of the measuring time, the Raman spectroscopy system 10 and the actuator 22 can be activated such that targeted measurements are conducted on the receptacles 62 in which biological objects are contained.

At least one Raman spectrum can be acquired on a receptacle 62 that contains no biological object 52, in order for example to at least partially compensate for the effect of the arresting unit 51 by difference spectrum formation. For this purpose, the Raman spectrum acquired on the empty receptacle 62 can be subtracted from a Raman spectrum assigned to a biological object 52. Weighting can be carried out in this subtraction in order to largely suppress the background signal of the arresting unit 62.

The device 1 can control the excitation laser and the image sensor of the Raman spectroscopy system 10 and the actuator 22 in accordance with the acquired positions of the biological objects 52 in order to selectively acquire Raman spectra on different biological objects 52 held in receptacles 62. Substances such as active substances, toxins, chemicals or other substances can be conveyed from the supply unit 30 to the arresting unit 51 in order to observe the reaction of the biological objects 52 to the substance(s).

Figure 4:
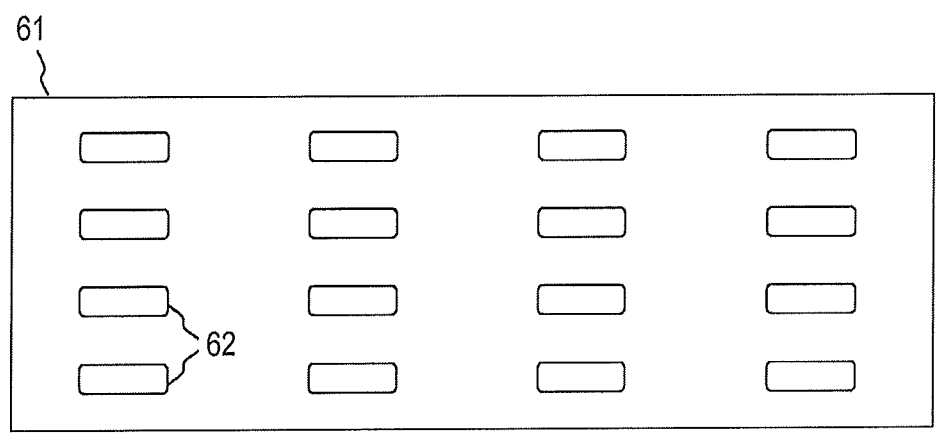
FIG. 4 is a top view of the arresting unit of FIG. 3.

In both the arresting unit 51 of FIG. 3 and the arresting unit 61 of FIG. 4, the biological objects arrested by the arresting unit can retain residual motility in the corresponding receptacles. In order to carry out Raman spectroscopy, by means of the interplay between the arresting unit and an optical trapping potential, which can be provided for example by the excitation beam of the Raman spectroscopy system 10 itself, the biological objects can be maintained in a position in order to allow acquisition of the Raman spectra and/or improve the quality of the Raman data.

FIG. 4 shows a top view of a configuration of the arresting unit 62. The receptacles 62, which can be configured as recesses, can be provided in a regular arrangement. Channels can connect a plurality of receptacles in order to facilitate the supply of substances to a plurality of biological objects so as to determine these substances by Raman spectroscopy.

Each receptacle 62 of the arresting unit 61 can be configured such that it can accommodate only exactly one biological object of a specified type, for example only one cell of a cell type. In other configurations, the receptacles can also be configured such that they can accommodate a plurality of biological objects of a specified type, as shown in FIG. 5.

Figure 5:
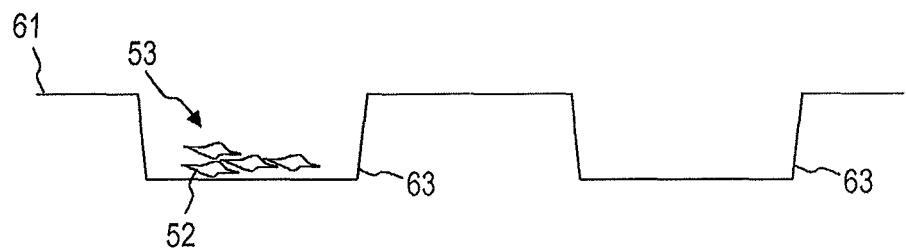
FIG. 5 shows biological objects on an arresting unit of a device according to an example.

FIG. 5 is a sectional view of an arresting unit 61 according to a further example. The arresting unit 61 can be configured as a microwell plate or another device comprising a plurality of receptacles 63 for accommodating biological objects. The receptacles 63 can each be configured as recesses, for example as microwells.

The receptacles 63 can have a depth and/or lateral dimensions that are adapted to the dimensions of the biological objects to be measured. For example, the receptacles 63 can be dimensioned such that only one cell of the desired cell type each can be accommodated in the receptacle 63. The receptacles 63 can be dimensioned to accommodate cell clusters or cell clones 53 comprising a plurality of cells 52.

The receptacles 62, 63 of the arresting unit 61 serve as holding areas configured to at least temporarily arrest biological objects.

Figure 6:
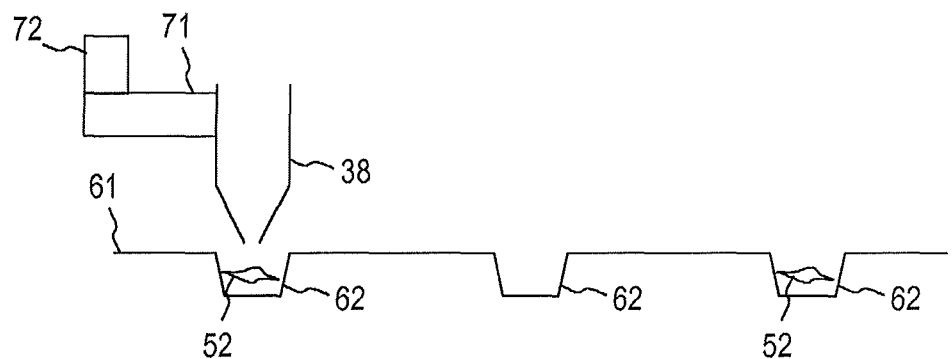
FIG. 6 is a view of an arresting unit and a supply unit of a device according to an example.

FIG. 6 shows a partial view of the device 1, which can be used in combination with each of the different arresting units. A supply element 38 of the supply unit 30 is configured to supply a substance or a plurality of substances to a biological object or a plurality of biological objects arrested by the arresting unit. The supply element 38 can comprise a nozzle through which an active substance, a toxin, a chemical or another substance is emitted. The supply element 38 can be connected via the conveying unit 36 to at least one reservoir 34, 35.

The supply unit can comprise one or a plurality of microfluid channels through which a substance is guided onto a plurality of cells or cell clusters. A plurality of channels can be present next to one another, wherein the supply unit can be configured to administer similar or different substances via the plurality of channels.

The device 1 can comprise a further actuator 72 in order to produce a relative movement between the arresting unit 61 and the supply element 38. The further actuator 72 can be actuable independently of the actuator 22. The further actuator 72 can be configured to move the supply element 38 relative to the arresting unit 61 and/or move the arresting unit 61 relative to the supply element 38. The further actuator 72 can for example adjust a holder 71 for the supply element linearly in two or three orthogonal spatial directions.

Channels can be present in the arresting unit 61 in order to connect a portion of the receptacles 62 to one another so that the substance supplied via the supply element 38 is conveyed further to biological objects in a plurality of receptacles 62. In this manner, the measurement statistics can be improved.

Figure 7:
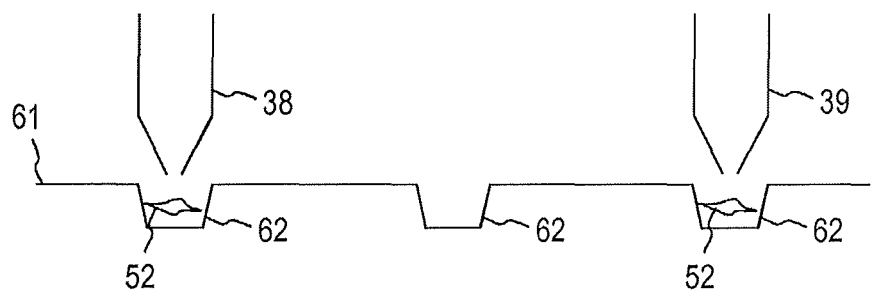
FIG. 7 is a view of an arresting unit and a supply unit of a device according to an example.

FIG. 7 shows a partial view of the device 1, which can be used in combination with each of the different arresting units. A supply element 38 of the supply unit 30 is configured to supply a substance or a plurality of substances to a biological object or a plurality of biological objects arrested by the arresting unit. A further supply element 39 is configured to supply a further substance. The supply elements 38, 39 can supply different substances. The supply element 38 and the further supply element 39 can each comprise a nozzle through which the active substance, a toxin, a chemical or another substance is emitted. The supply element 38 can be connected via the conveying unit 36 to at least one reservoir 34. The further supply element 39 can be connected via the conveying unit 36 to at least one further reservoir 35.

The supply unit 30 can be configured to supply the same or different substances to a plurality of different biological objects in parallel via the supply elements 38, 39. For example, the biological objects can be subdivided by the computing unit 40 or in a user-defined manner into a plurality of groups comprising a first group and a second group, each containing a plurality of biological objects. A first substance can be supplied via the supply element 38 to the biological objects of the first group. A second substance can be supplied via the further supply element 39 to the biological objects of the second group. The respective reaction of the biological objects of the two groups to the different substances can be investigated by Raman spectroscopy.

The arresting unit 61 can comprise channels that connect parts of the receptacles 62 with one another so that the substance supplied via the supply element 38 is further guided to biological objects in a plurality of receptacles 62. The channels can define a plurality of groups of receptacles 62 disconnected from one another, for example, a first group of receptacles connected with one another, and separately therefrom, a second group of receptacles connected with one another.

The Raman spectra that are assigned to biological objects can be acquired by Raman spectroscopy on the biological objects themselves. Alternatively or additionally, Raman spectra that are assigned to biological objects can also be acquired on a fluid at least partially covering the biological objects, for example a liquid. In this manner, metabolites or other substances discharged by the biological objects can be acquired by Raman spectroscopy in order to determine the reaction to a substance.

Figure 8:
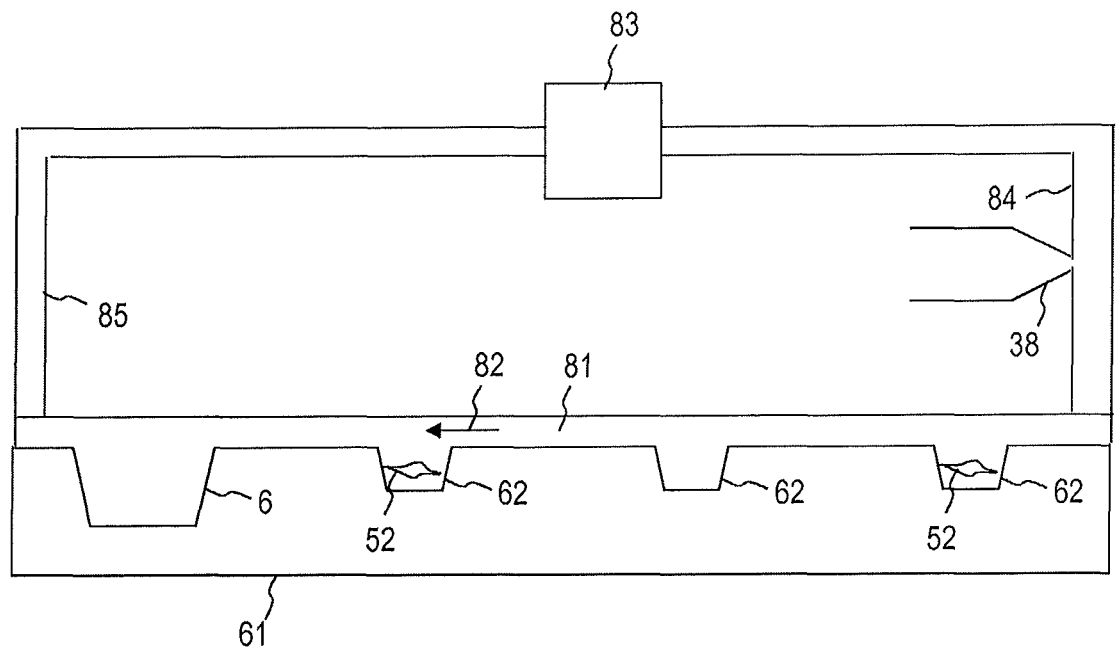
FIG. 8 is a view of an arresting unit and a supply unit of a device according to an example.

FIG. 8 shows a partial view of the device 1, which can be used in combination with each of the different arresting units. Receptacles 62 of the arresting unit 61 are at least partially covered by a fluid 81.

The arresting unit 61 can comprise a collection receptacle 6 or a plurality of collection receptacles. The collection receptacle(s) 6 can be configured in the microfluidic chip. Cells can be brought from the receptacles 62 via the fluid stream into the collection receptacle(s) 6.

The transfer from a receptacle 62 into the collection receptacle 6 can comprise movement of the cell from the receptacle 62 into the flow of the fluid 81, transportation of the cell in the flow of the fluid 81, and movement of the cell from the flow of the fluid 81 into the collection receptacle 6. The movement from the receptacle 62 into the flow of the fluid 81 and/or the movement from the flow of the fluid 81 into the collection receptacle 6 respectively can be implemented using optical means, in particular a mobile optical trap.

A decision as to which of a plurality of collection receptacles is to be used to collect a cell can be made in accordance with Raman spectra previously acquired in the receptacle 62. Alternatively or additionally, a decision as to whether a cell is to be collected in a collection receptacle 6 at all can be made in accordance with Raman spectra previously acquired in the receptacle 62. The corresponding decision can be automatically made by the device 1 in accordance with the previously acquired Raman spectra.

Cells can be collected by the collection receptacles 6 in accordance with their properties.

The device 1 can be configured to move the fluid 81 into a fluid stream. The fluid 81 can be a liquid.

The device 1 can comprise, for example, a pump 83 or another device for generating a flow speed of the fluid 81. At least one channel 84, 85 can be provided for supplying of the fluid by the arresting unit 61 and/or for discharging of the fluid by the arresting unit 61.

Biological objects 52 can be transported in the fluid 81. The device 1 can comprise a device for selective movement of biological objects between a fluid stream 82, which flows over at least one part of the receptacles 62, and the receptacles 62. The device can comprise optical tweezers or other electrical and/or magnetic fields or waves by means of which biological objects 52 are moved between the fluid stream 82 and the receptacles 62.

The fluid stream 82 need not necessarily be implemented as a closed fluid circuit. For example, the fluid stream 82 can be used in order to sort biological objects 52 in accordance with the acquired Raman spectra. Biological objects 52 can be transported by a controllable device for controlling the fluid stream 82 into a plurality of different receptacles independently of which reaction the biological objects show to a substance on the Raman spectra and/or in accordance with the type of biological object determined by means of Raman spectroscopy.

The supply of one of a plurality of substances can be integrated into the fluid stream 82. For example, a supply element 38 can comprise an outlet opening for the supply of one or a plurality of substances that is fluidly connected to a supply channel 84 for the fluid 81. By controlling the conveying unit 36, the concentration of the substance(s) 31, 32 in the fluid 81 can be controlled or regulated.

Figure 9:
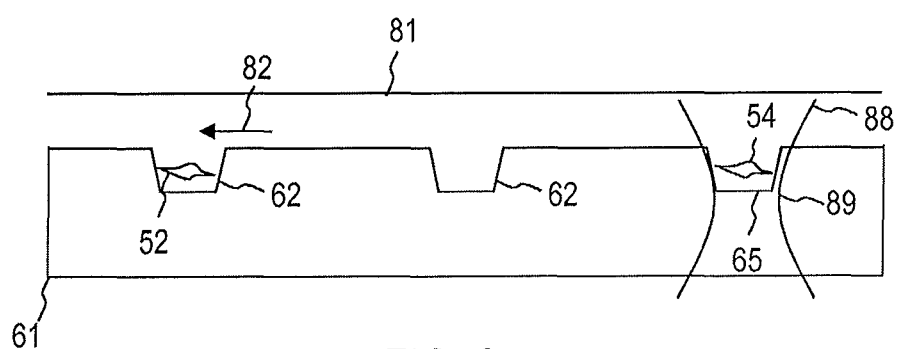
FIG. 9 shows biological objects on an arresting unit of a device according to an example.
Figure 10:
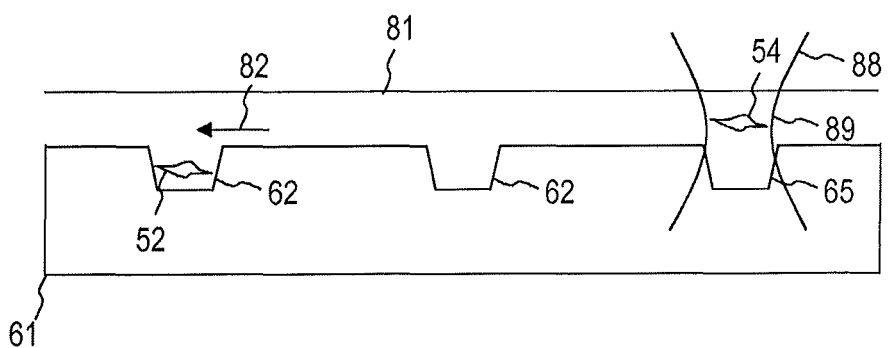
FIG. 10 shows biological objects on an arresting unit of a device according to an example.

FIG. 9 and FIG. 10 illustrate the functioning of a device for the selective movement of biological objects between the fluid stream 82 and the receptacles 62. The device for selective movement of biological objects can comprise optical tweezers. Such a radiation field 88 can comprise a focal area 89 that is moveable perpendicularly to a surface of the arresting unit 61.

The radiation field 88 can be generated by the excitation beam of the Raman spectroscopy system 10 or by a laser beam different therefrom.

By controlling the radiation field 88 such that the focal area 89 is moved perpendicularly to the plane of the arresting unit 61, a biological object 54 is moved between the fluid stream 82 and a receptacle 65, as shown in FIG. 10. In the receptacle 65, the biological object 54 may previously have been deposited from the fluid stream 82 due to the force of gravity. Optionally, the biological object 54 can be held in the receptacle 54 by the radiation field 88 and/or the edges of the receptacle 65. The radiation field 88 need not remain continuously activated in order to hold the biological object 54 in the receptacle 65. For example, the biological object can also be deposited in the receptacle 65 by the force of gravity after it has been flushed in by the fluid stream 82.

Optionally, the biological object 54 can be moved from the fluid stream 82 into the receptacle 65 using an optical or other radiation field.

Alternatively or additionally, accommodation of cells in the receptacles 62, 65 can be carried out in that the cells are flushed through the fluidic channel and deposited in the receptacles 62, 65 by gravity. Such a transfer of the receptacles 62, 65 into the fluid stream can be carried out with an optical trap, by means of other electromagnetic fields or waves, by selective exertion of fluid pressure, or in other ways. The cells can then be transferred from the fluid stream into the collection receptacles of the microfluidic chip.

Instead of or in addition to an optical radiation field 88, other electrical, magnetic or electromagnetic fields or waves can be used to move a biological object 65 between the fluid stream 82 and a receptacle 62, 65. Independently of the specific implementation of the device for selective movement of biological objects, the device 1 can be configured such that the biological objects can be reversibly transferred in a non-destructive manner from the fluid stream 82 into a receptacle 65 and from the receptacle 65 back into the fluid stream 82.

Further configurations of arresting units can be used in devices and methods according to the examples.

Figure 11:
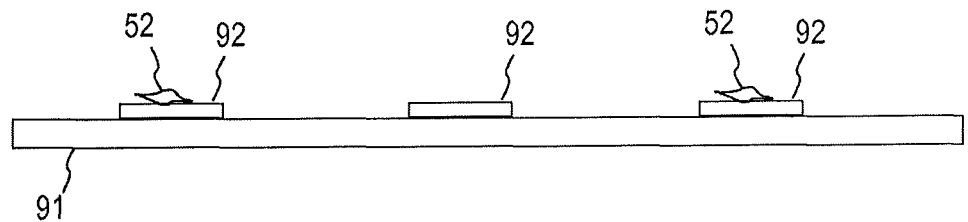
FIG. 11 shows biological objects on an arresting unit of a device according to an example.
Figure 12:
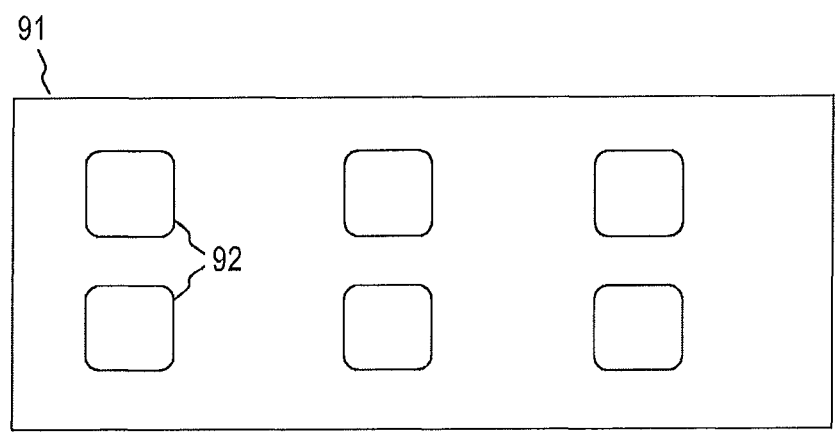
FIG. 12 is a top view of the arresting unit of FIG. 11.

FIG. 11 shows a sectional view of an arresting unit 91, and FIG. 12 shows a top view of the arresting unit 91. The arresting unit 91 comprises areas 92 that are arranged on a surface of the arresting unit 91 in a structured manner. The areas 92 can be coatings or have another configuration. The areas 92 are configured to at least temporarily arrest biological objects 52 on them. The areas 92 can be provided in a regular or irregular arrangement.

In use of the arresting unit 91, the device 1 can automatically detect the positions of the areas 92. For this purpose, the computing unit 40 can automatically evaluate the image acquired by the image acquisition device 19 in order to determine a position and type of the areas 92 of the arresting unit 91.

The device 1 can further be configured to automatically detect in which of the areas 92 biological objects 52 are positioned. For this purpose, for example, contrast, autofluorescence, or fluorescence labelling of the biological objects 52 can be used. For this purpose, the device 1 can comprise a light source for excitation of the autofluorescence or fluorescence. The positions of the respective areas 92 in which a biological object is positioned can be stored in a storage element of the computing unit 40. For optimum utilization of the measuring time, the Raman spectroscopy system 10 and the actuator 22 can be activated such that selective measurements are carried out on the areas 92 at which biological objects are arrested.

At least one Raman spectrum can be acquired on an area of the arresting unit 92 that contains no biological object 52, for example in order to at least partially compensate for the influence of the arresting unit 91 by difference spectrum formation.

The device 1 can control the excitation laser and the image sensor of the Raman spectroscopy system 10 and the actuator 22 in accordance with the acquired positions of the biological objects 52 in order to selectively acquire Raman spectra on different biological objects 52 that are arrested on the areas 92. Substances such as active substances, toxins, chemicals or other substances can be conveyed from the supply unit 30 to the arresting unit 91 in order to observe the reaction of the biological objects 52 to the substance(s).

Figure 13:
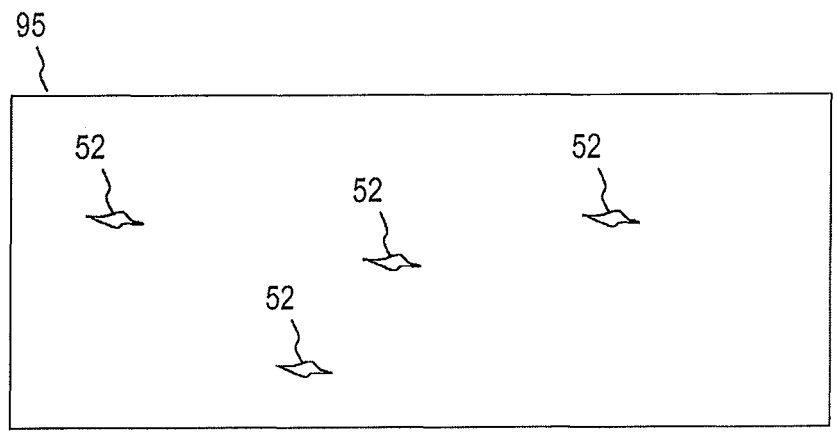
FIG. 13 is a top view of an arresting unit of a device according to an example.

FIG. 13 shows an arresting unit 95 having a surface on which the biological objects 52 can adherently grow. The arresting unit 95 can comprise a homogeneous or structured coating that can facilitate the growth of the biological objects.

The arresting unit 95 can be a matrix mixed with cells, such as an incubated matrix in which the cells are randomly distributed. The device 1 can automatically locate the position of the cells by image detection. For this purpose, either the contrast, autofluorescence, or fluorescence of the cells can be evaluated.

In each of the arresting units described with reference to FIGS. 2 through 13, biological objects can be transported and optionally sorted in a fluid stream, as was described with reference to FIGS. 8 through 10.

With reference to FIGS. 14 through 23, techniques are described that can be automatically carried out by the device 1 in order to automatically determine the reaction of biological objects to a substance or a plurality of different substances and/or determine the type of biological objects, for example in order to identify a bacterium or a cell type.

Figure 14:
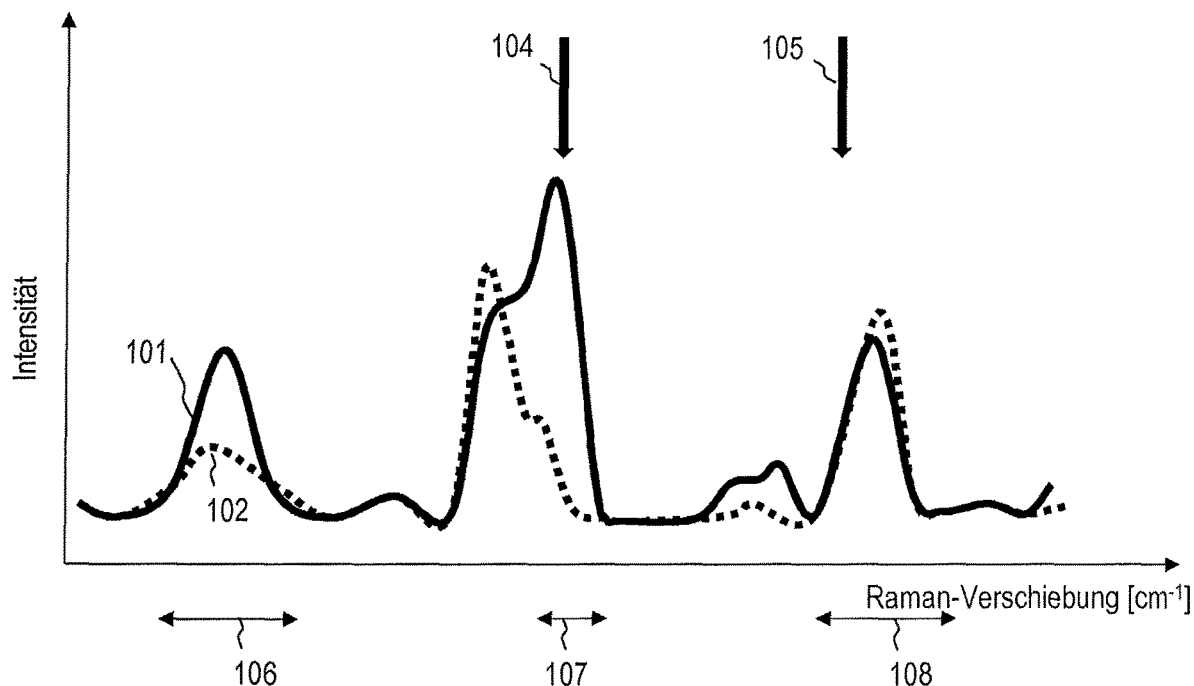
FIG. 14 shows the evaluation of Raman spectra for analyzing a reaction of a biological object to a substance according to an example.

FIG. 14 shows Raman spectra 101, 102 for a biological object. A first Raman spectrum 101 can be acquired before administration of a substance. At least one second Raman spectrum 102 can be acquired during or after administration of the substance. Based on the shift in wave numbers at which Raman peaks are present, and/or by means of the spectral weight of different Raman peaks 104, 105, it can be determined whether or not the biological object shows a reaction to the substance. These differences can be used by the device 1 for automatic determination of the reaction of the biological object to the substance, for example, for detection of drug resistance.

Various wave numbers or wave number intervals 106, 107, 108 can be evaluated in order to determine the reaction of the biological object. For example, the Raman spectra in one or a plurality of the wave number intervals 813-832 cm$^{-1}$, 864-888 cm$^{-1}$, 911-920 cm$^{-1}$, 984-1070 cm$^{-1}$, 1038-1051 cm$^{-1}$, 1078-1091 cm$^{-1}$, 1100-1131 cm$^{-1}$ and/or 1430-1443 cm$^{-1}$ can be evaluated in order to detect a transition from living to apoptotic states of biological objects. This can be relevant both for determination of the compatibility of chemical substances and for the determination of drug resistance.

The device 1 can acquire patterns of the spectra and use and optionally determine differences in the patterns as discrimination values. Examples of such patterns include one or a plurality of peak positions, peak heights, steepness of the flanks, shape and position of the valleys between the peaks, and/or other variables that can be derived from the spectrum.

The Raman spectrum or the Raman spectra can be further processed by the computing unit 40. For example, the computing unit 20 can carry out a cluster analysis, a main component analysis, or an LDA of the acquired Raman spectra. Signal components of the arresting unit can be at least partially eliminated from such an analysis by difference spectrum formation.

The result of the cluster analysis can be used in order to quantitatively analyze reactions and the speed of reactions of biological objects to one or a plurality of substances.

Figure 15:
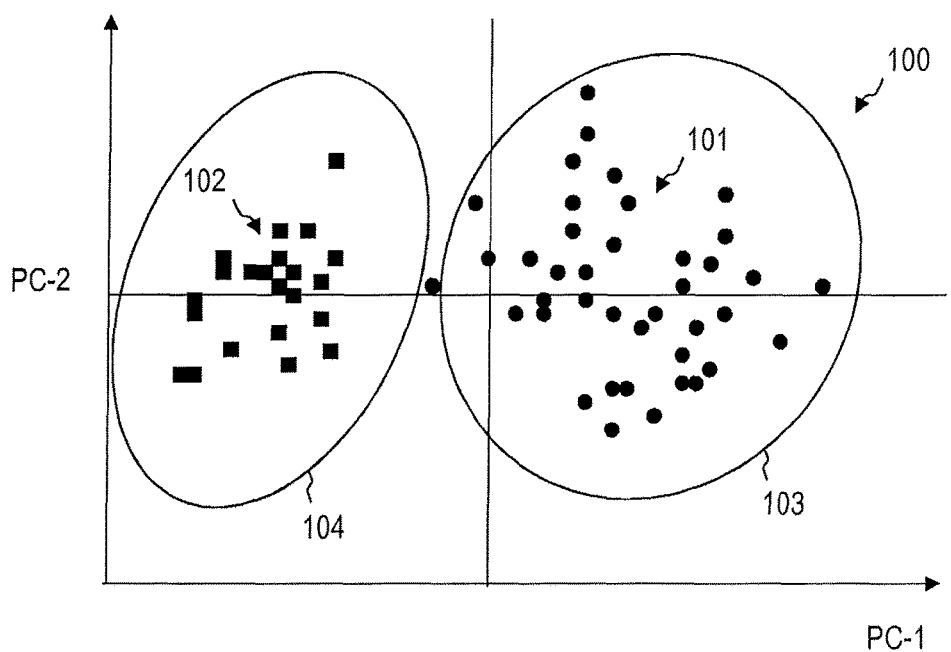
FIG. 15 shows results of a main component analysis in an evaluation of Raman spectra for analyzing a reaction of a biological object to a substance according to an example.

FIG. 15 shows examples of results 100 of a main component analysis carried out by the computing unit 40 in order to determine whether a biological object shows a reaction to administration of a substance. In this context, the main component analysis is carried out for a Raman spectrum or a plurality of Raman spectra acquired on the same biological object 3, 4. The data points are shown according to a pair of the different main components PC-1 and PC-2. FIG. 15 shows the data points 101 that are assigned to living cells and the data points 102 that are assigned to apoptotic cells. Comparable data points can result from an altered functional state of the cells after active substance administration. Similar structures are also produced in a main component analysis of the Raman spectra of other biological objects such as microbes, e.g. bacteria.

The result of the main component analysis of the Raman spectra acquired on the biological objects can be evaluated as to whether and how many data points lie in different regions 103, 104 of the coordinate system spanned by a plurality of main components. For example, it can be determined how many data points lie in a region 103 that is assigned to living cells of a specified cell type. It can be determined how many data points lie in a region 104 that is assigned to apoptotic cells of the same cell type. It can be determined how many data points lie in further regions of a coordinate system spanned by a plurality of main components that are assigned to other biological objects and/or other functional states of the biological objects.

As can also be seen in FIG. 15, the data points obtained by the main component analysis shift depending on whether and in what way a biological object reacts to a substance. Accordingly, by means of the main component analysis of one Raman spectrum or a plurality of Raman spectra, the computing unit 40 can automatically determine which cell types are present and/or whether the cells transition to an apoptotic state as a reaction to different substances.

Figure 16:
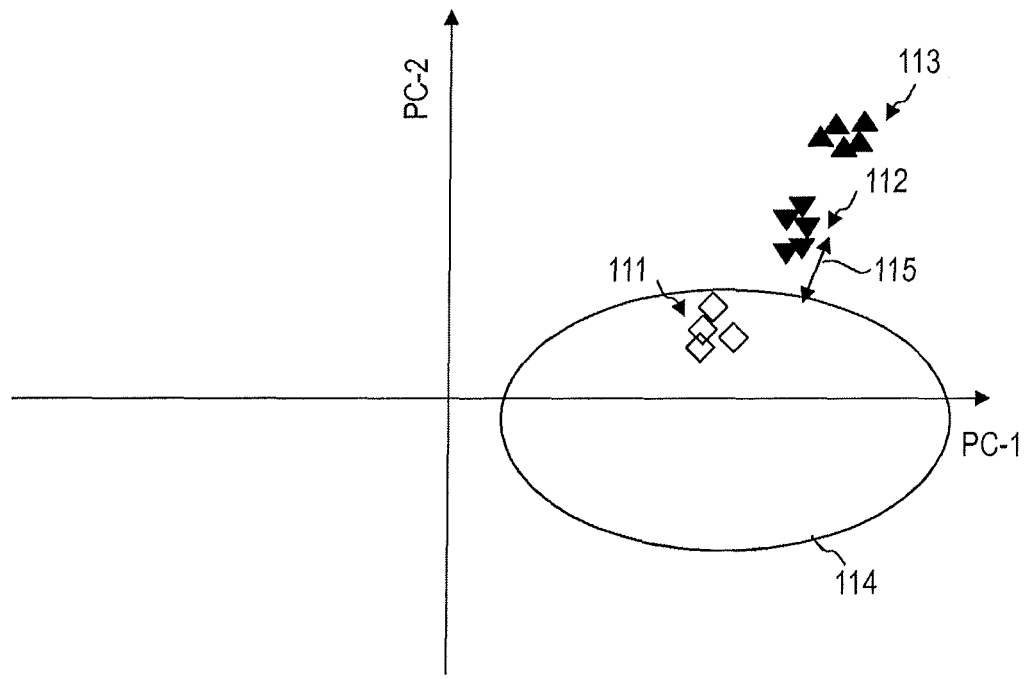
FIG. 16 shows results of a main component analysis in an evaluation of Raman spectra for analyzing a reaction of a biological object to a substance according to an example.

FIG. 16 illustrates evaluation of the kinetics of a reaction of a biological object to a substance. Also shown is the result of a main component analysis. Before administration of a substance, the data points 111 of a main component analysis of the Raman spectrum of a biological object lie in an area 114 of the space spanned by the main components. The area 114 corresponds to functionally intact biological objects, for example functionally intact living cells or bacteria.

As a reaction to administration of the substance, for example a toxin or an active substance, a shift in the data points takes place. After a first period following administration of the substance, the data points 112 determined by main component analysis of the Raman spectrum of a biological object may have left the area 114. This shows that a functional change, for example by transition to an apoptotic state, takes place.

After a second period following administration of the substance, which is longer than the first period, the data points 113 determined by main component analysis of the Raman spectrum of a biological object may have moved farther away from the area 114 in the main component space.

A distance 115 between the data points 112, 113 and the boundary of the area 114 in the main component space can be determined in a time-dependent manner in order to detect functional changes of biological objects as a reaction to administration of the corresponding substance.

Such processing can be carried out not only for one substance, but also in parallel for the administration of a plurality of different substances. In this context, different biological objects of the same type can be supplied in order to obtain data on the kinetics of the reaction to the substance from the Raman spectra.

By comparing the two spectra before and after the administration of an active substance, the device 1 can also determine which type of molecules are relevant for the change in the Raman spectrum. For this purpose, one can use difference spectra, such as so-called "loadings," and/or matching with data on spectra stored in a database and/or a comparison of the Raman characteristics of various molecules documented in the literature.

Other processing methods can be automatically applied by the computing unit 40. For example, an LDA or a cluster analysis can be carried out in order to determine the reaction of biological objects to one or a plurality of substances.

Figure 17:
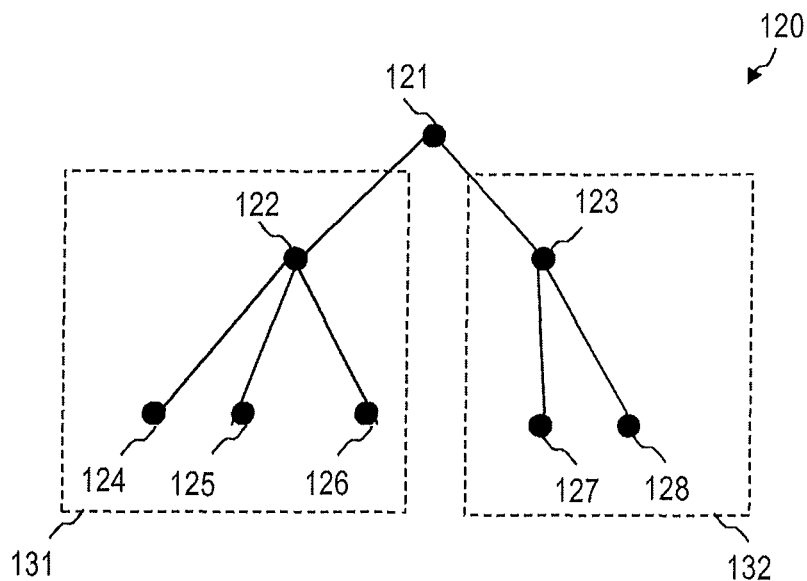
FIG. 17 shows a cluster analysis of Raman spectra for analyzing a reaction of a biological object to a substance according to an example.

FIG. 17 is a schematic illustration of the functioning of the computing unit 40 of the device 1 in such a statistical evaluation, which comprises a cluster analysis.

By evaluation of a plurality of Raman spectra that are assigned to different reactions of biological objects to different substances, a tree 120 of Raman spectra is constructed either by the computing unit 40 of the device 1 itself or far from the device 1. The tree 120 contains a plurality of nodes 121-128. Raman spectra are assigned to the nodes 121-128 according to a degree of similarity that for example can be based on a cosine distance.

The tree 120 can comprise a first subtree 131 that is assigned to living biological objects. The tree 120 can comprise a second subtree 132 that is assigned to apoptotic biological objects or other functionally altered biological objects.

In evaluation of one Raman spectrum or a plurality of Raman spectra that were acquired on biological objects 3, 4 during or after administration of a substance, the computing unit 40 of the device 1 can in each case use the distance measurement in order to calculate to which of the leaf nodes 124-128 and/or the inner nodes 122, 123 of the tree 120 the corresponding Raman spectrum is to be assigned.

In this manner, Raman spectra can be assigned to different reactions to administration of a substance even without prior knowledge of individual relevant wave numbers. For example, Raman spectra acquired on an apoptotic cell of a specified type can be assigned to at least one of the various leaf nodes 124-128. Raman spectra acquired on a living cell of the same type can be assigned to at least one more of the different leaf nodes 124-128.

In order to differentiate among different reactions of biological objects to substances, the Raman spectrum of each biological object on which measurement is conducted can generally comprise a number N of intensities at different wavelengths. The number N can be greater than one, in particular much greater than one. By means of hierarchical clustering, for example, in an N-dimensional space, one can take advantage of the fact that in this space, biological objects that show similar behavior are closer to one another than biochemically distant cells. By means of the hierarchical clustering, biological objects that are close to one another in their behavior and thus form a cluster can be distinguished from other objects located farther from one another. The biological objects are sorted into natural clusters or groups due to their position in the data space.

Figure 18:
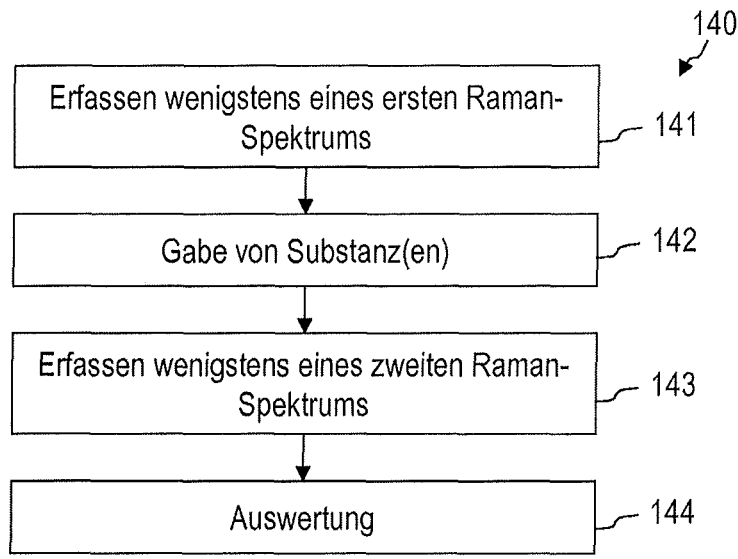
FIG. 18 is a flow diagram of a method according to an example.

FIG. 18 is a flow diagram of a method 140 according to an example. The method can be automatically carried out by the device 1 according to an example.

In step 141, at least one first Raman spectrum of a biological object is acquired before administration of a substance. In this context, the biological object can be arrested by the arresting unit.

In step 142, a substance is supplied to the biological object. The substance can be selected from an active substance, a chemical, a toxin, or another substance.

In step 143, at least one second Raman spectrum of the same biological object is acquired during or after administration of the substance. The actuator 22 of the device 1 can be controlled such that the same biological object as in step 141 is again engaged in order to acquire the at least one second Raman spectrum during or after administration of the substance.

In the acquisition of the first Raman spectrum in step 141 and/or the acquisition of the at least one second Raman spectrum in step 143, the biological object can be moved by optical tweezers or another electrical or magnetic alternating field between a fluid stream and a holding area of the arresting unit in order to arrest the biological object for the measurements.

The acquisition of the first Raman spectrum in step 141 and/or the acquisition of the at least one second Raman spectrum in step 143 can include Raman scattering on the corresponding biological object itself. The acquisition of the first Raman spectrum in step 141 and/or the acquisition of the at least one second Raman spectrum in step 143 can alternatively or additionally include Raman scattering on a supernatant, for example the fluid 82 covering the biological object, or another material at least partly surrounding the biological object.

In step 144, an evaluation of the first Raman spectrum and/or at least one second Raman spectrum of the biological object can take place. By means of the evaluation, the reaction of the biological object to the substance can be determined. The evaluation can comprise a main component analysis, a cluster analysis, and/or an LDA, as described with reference to FIGS. 1 through 17. The evaluation can optionally comprise the suppression of signal components caused by the arresting unit. For this purpose, at least one Raman spectrum of the arresting unit can be acquired in an area without a biological object, as described in further detail with reference to FIG. 19. The at least one Raman spectrum of the arresting unit can be subtracted from the first Raman spectrum acquired in step 141 and/or the at least one second Raman spectrum acquired in step 142 in order to separate signal components of the arresting unit from the signal of the biological object.

Figure 19:
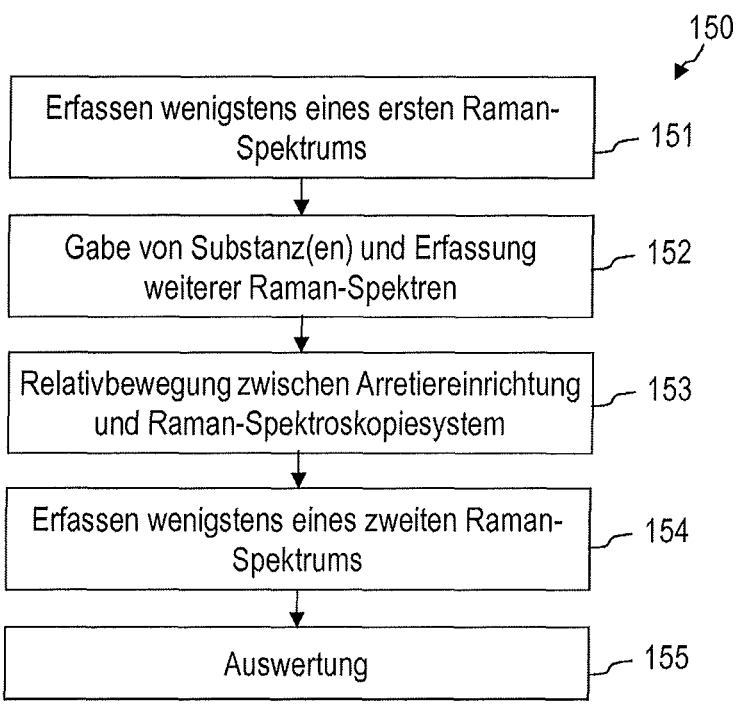
FIG. 19 is a flow diagram of a method according to an example.

FIG. 19 is a flow diagram of a method 150 according to an example. The method can be automatically carried out by the device 1 according to an example.

In step 151, at least one first Raman spectrum of a biological object is acquired while the biological object is arrested by the arresting unit. The first Raman spectrum can be acquired before, during or after administration of a substance, for example, an active substance or a chemical.

In step 152, a substance can be supplied, for example an active substance or a chemical. For this purpose, the substance can be transported via a laminar or non-laminar flow to the biological objects. Further Raman spectra can then be acquired.

In steps 151, 152 and optionally the following steps, a cell or another biological object can initially be measured by Raman scattering, and another cell can then be engaged. After administration of an active substance or another substance and a waiting time, all of the cells already examined by Raman spectroscopy can again be individually engaged and subjected to further Raman spectroscopy after the substance has been allowed to act on the biological objects for at least a predetermined waiting time.

In step 153, the actuator 22 can be controlled in order to produce a relative movement between the arresting unit and the Raman spectroscopy system. The actuator 22 can be controlled such that in the subsequently conducted acquisition on the arresting unit, no biological object is excited by the Raman spectroscopy system. The control of the actuator 22 can be carried out such that the arresting unit is positioned in the excitation beam.

In step 154, at least one second Raman spectrum can be acquired, wherein no biological object is positioned in the excitation beam of the Raman spectroscopy system 10. The at least one second Raman spectrum can represent the Raman scattering on the arresting unit itself.

In step 155, an evaluation can be carried out in which the electronic computing unit 40 suppresses the signal components from the arresting unit in the at least one first Raman spectrum by forming a difference spectrum between the at least one first Raman spectrum, in which a biological object is positioned in the excitation beam, and the at least one second Raman spectrum, in which no biological object is positioned in the excitation beam. Weighted subtraction can be carried out in which the second Raman spectrum, which was acquired only on the arresting unit, is multiplied by a weighting factor different from one before it is subtracted from the first Raman spectrum. The weighting factor can be determined by comparing the height of a characteristic peak for the arresting unit in the first Raman spectrum and in the second Raman spectrum.

The evaluation described for step 155 can be carried out as part of the determination of the reaction of biological objects to a substance in step 144.

Figure 20:
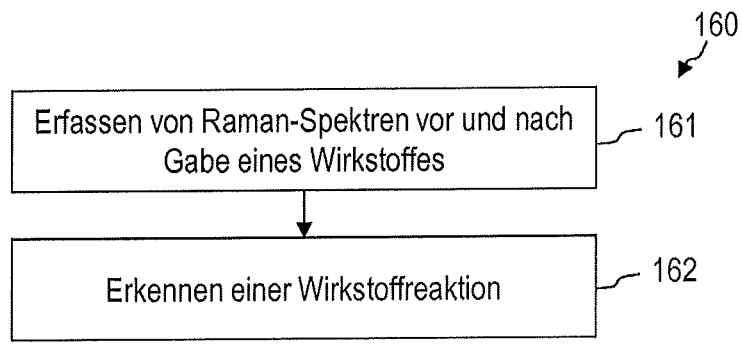
FIG. 20 is a flow diagram of a method according to an example.
Figure 21:
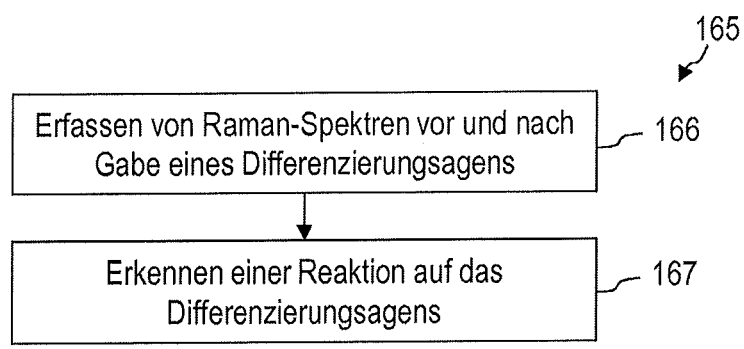
FIG. 21 is a flow diagram of a method according to an example.
Figure 22:
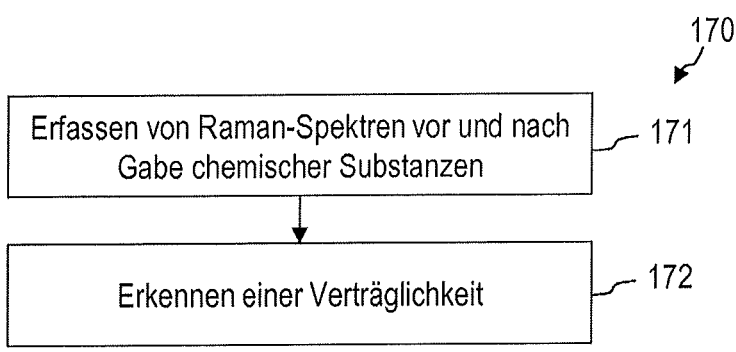
FIG. 22 is a flow diagram of a method according to an example.

The methods and devices according to different examples can be used for different purposes, as shown for example in FIGS. 20 through 22.

FIG. 20 is a flow diagram of a method 160 according to an example. The method can be automatically carried out by the device 1 according to an example. The method can be used for the determination of drug resistance and/or for another type of determination of suitable active substances.

In step 161, Raman spectra of a biological object or a plurality of biological objects are acquired before an active substance is added and during or after the active substance is added. The active substance can comprise an antibiotic.

In step 162, reactions of cells to the active substance are detected by evaluation of the acquired Raman spectra. For this purpose, it can be determined whether microbes or cells transition to a functionally altered and/or impaired state as a reaction to the active substance. The transition to such a state can be detected by a main component analysis, a cluster analysis, an LDA, or other statistical evaluation methods.

An example of the reaction of the cell or another biological object to an active substance can be that drug resistance of the biological object is detected by means of the method.

Alternatively or additionally, for example, it can be detected in step 162 whether the cell transitions into a functionally altered state after administration of differentiating substances. For example, the conversion from a toti- or multipotent state to a functionally altered state can be detected.

The transition to such a state can be detected by a main component analysis, a cluster analysis, an LDA, or other statistical evaluation methods.

FIG. 21 is a flow diagram of a method 165 according to an example. The method can be automatically carried out by the device 1 according to an example. The method can be used for determination of a reaction to a differentiating agent.

In step 165, Raman spectra of a biological object or a plurality of biological objects are acquired before a differentiating agent is added and during or after the differentiating agent is added.

In step 166, it is detected by evaluation of the acquired Raman spectra whether a cell transitions to an altered state after administration of differentiating substances. For example, the transition from a toti- or multipotent state to a functionally altered state, for example a differentiated state, can be detected. The transition to such a state can be detected by a main component analysis, a cluster analysis, an LDA, or other statistical evaluation methods.

FIG. 22 is a flow diagram of a method 170 according to an example. The method can be automatically carried out by the device 1 according to an example. The method can be used for determination of the compatibility of chemicals or other substances.

In step 171, Raman spectra of a biological object or a plurality of biological objects are acquired before a chemical is added and during or after the chemical is added.

In step 172, the compatibility of the corresponding chemical is determined by evaluation of the acquired Raman spectra. For this purpose, it can be determined whether cells, cell clusters or cell clones, as a reaction to the chemical, are converted to a functionally impaired state, for example apoptosis. The transition to such a state can be detected by a main component analysis, a cluster analysis, an LDA, or other statistical evaluation methods.

Figure 23:
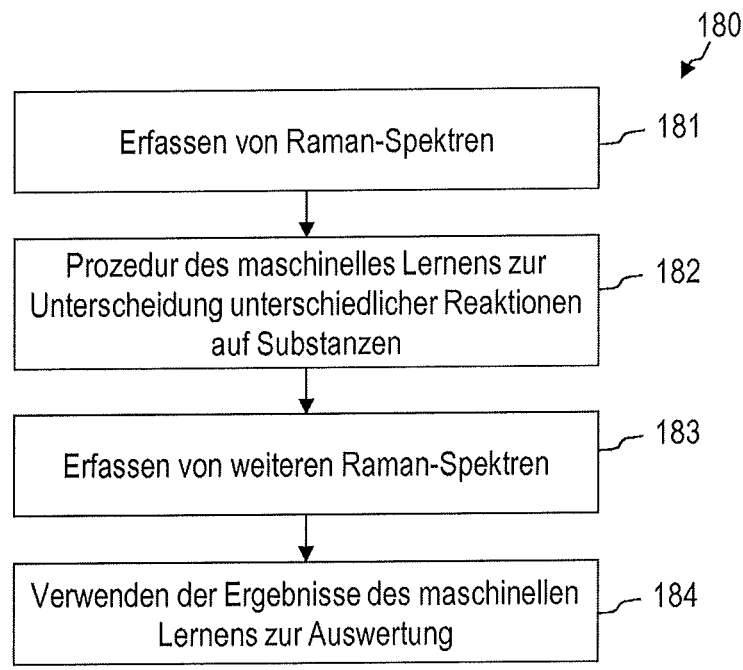
FIG. 23 is a flow diagram of a method according to an example.

FIG. 23 is a flow diagram of a method 180 according to an example. The method 180 can be carried out by the device 1. The method 180 can be used for determination of the reaction of biological objects to substances. Rules according to which the reaction of biological objects to substances is automatically assessed can be automatically learned by the device 1 using a machine learning method, in particular by supervised learning. The rules can be stored in a non-volatile manner in the storage element of the computing unit 40.

In step 181, a plurality of Raman spectra is acquired. By means of the plurality of Raman spectra, healthy and functionally impaired cells, microbes or other biological objects can be acquired.

In step 182, a procedure of machine learning is carried out. The procedure can be supervised learning. In this case, the device 1 can receive user input for different acquired Raman spectra.

The user input can assign Raman spectra, Raman peaks and/or clusters to a cluster analysis of different types of biological objects, for example, different cell types or different bacteria. The user input can assign Raman spectra, Raman peaks and/or clusters to a cluster analysis of different types of functional states, for example a living state and an apoptotic state.

Based on the user input, the device 1 can set one or a plurality of parameters of a set of rules by means of which the device 1 evaluates Raman spectra in order to assess the reaction of biological objects to substances. Based on the user input, for example, the computing unit 40 can adjust one or a plurality of parameters of a supporting vector machine by means of which the acquired Raman spectra are evaluated in order to assess the reaction of biological objects to substances.

The rules learned, for example the parameters of the supporting vector machine, can be stored by the device 1 in the storage element 43.

In step 183, Raman spectra can be acquired on a biological object to be tested to which a substance is supplied.

In step 184, the stored rules can be applied to the Raman spectra acquired in step 183. This can for example be carried out as described with reference to FIGS. 15 through 17. Based on the rules, it can be determined from the acquired Raman spectra which cell types or microbes are present. Based on the rules, one can determine from the acquired Raman spectra whether biological objects are subject to functional changes compared to fully functional biological objects.

In this manner, a plurality of classes or clusters can be identified. By comparing the spectra in each class with the spectra of already identified cells, for example, from a pure culture of melanocytes or other relevant cells, each class can be assigned a cell type. The number of cells in each class can be used for determination of the quantitative ratios. The number of cells in each class divided by the total number of spectra measured can then quantitatively indicate the proportion of the respective cell type in the material, for example in an apoptotic state.

The device and the method according to the examples can be configured such that in a multiplex technique, the Raman spectra of a plurality of biological objects can be acquired in parallel, in particular simultaneously. For this purpose, an excitation beam can be split into a plurality of excitation beams, as described in further detail by means of FIGS. 24 through 27.

Figure 24:
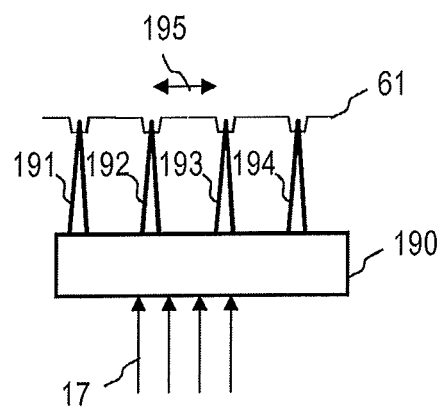
FIG. 24 shows a schematic sectional view of an arresting unit and the splitting of an excitation beam of a device according to an example.

FIG. 24 illustrates the production of a multiple configuration for the simultaneous acquisition of a plurality of Raman spectra. An optical element 190 is configured to convert an excitation beam 17 of the Raman spectroscopy system 10 to a plurality of excitation beams 191-194. The optical element 190 can comprise a spatial light modulator, one or a plurality of diffractive elements, or other units. The optical element 190 can be electronically controllable in order to set the number and/or arrangement of the plurality of excitation beams 191-194. The device 1 can be configured to activate the optical element 190 in accordance with the configuration of the arresting unit 61.

Each of the plurality of excitation beams 191-194 can generate an optical trap, for example as described above, in which a biological object is held for Raman spectroscopy. The biological object can be a single cell. Each of the plurality of excitation beams 191-194 can thus be used both to generate an optical trap and to excite Raman scattering.

The optical element 190 can be activated such that the plurality of optical traps is positioned in different microwells of the arresting unit 61, which can be a microfluidic chip. The plurality of excitation beams 191-194 can be produced such that their distance is coordinated with a distance 195 between the volume centers of the arresting areas, which for example can be microwells of a microfluidic chip.

A multiple configuration, in which, at the same time, each of a plurality of biological objects is excited by an excitation beam assigned to it respectively, can also be used in cases where a plurality of biological objects is held in a recess of the arresting unit 61, which can be a microfluidic chip. The plurality of optical traps can then define a regular or irregular arrangement of biological objects during Raman spectroscopy.

Figure 25:
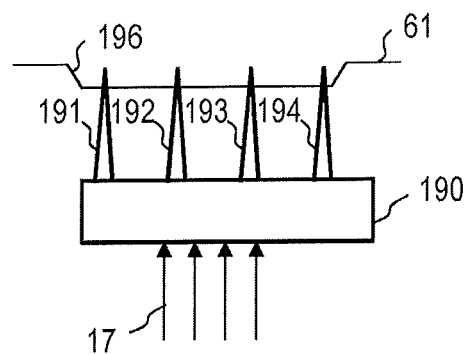
FIG. 25 shows a schematic sectional view of an arresting unit and the splitting of an excitation beam of a device according to an example.

FIG. 25 shows the production of a multiple configuration for the simultaneous acquisition of a plurality of Raman spectra. The optical element 190 is configured to convert an excitation beam 17 of the Raman spectroscopy system 10 into a plurality of excitation beams 191-194. The optical element 190 can comprise a spatial light modulator, one or a plurality of diffractive elements, or other units. The optical element 190 can be electronically controllable in order to set the number and/or arrangement of the plurality of excitation beams 191-194.

Each of the plurality of excitation beams 191-194 generates an optical trap in which a biological object is held in a recess 196 for Raman spectroscopy, as described above. Each of the plurality of excitation beams 191-194 holds a biological object assigned to it in an optical trap and serves to excite Raman scattering.

The optical element 190 can be activated such that the plurality of optical traps is positioned at different distances in the recess 196 of the microfluidic chip 2. The plurality of excitation beams 191-194 can be generated in such a way that their distance is adapted to an average size of the biological objects held in the recess 196.

Figure 26:
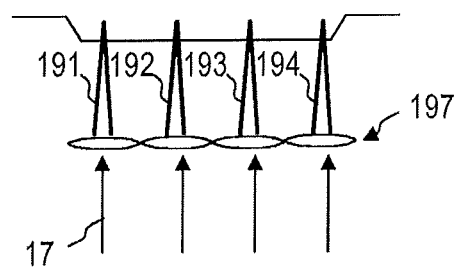
FIG. 26 shows a schematic sectional view of an arresting unit and the splitting of an excitation beam of a device according to an example.

FIG. 26 shows an implementation of the optical element 190 that can be used in devices according to the examples. The optical element 190, which is positioned in the optical path of the excitation beam 17, can be a diffractive element or comprise a diffractive element. The optical element 190 can comprise an arrangement 197 of a plurality of diffractive elements. The optical element 190 can be an array 197 of diffractive elements.

Alternatively or additionally, the optical element 190 can comprise an electrically controllable device. The electrically controllable device can be a spatial light modulator or another device that is controllable in order to produce various patterns of optical traps.

A configuration in which one excitation beam 17 is split into a plurality of excitation beams 191494 allows the simultaneous excitation of Raman scattering in a plurality of biological objects, which are held in the optical traps of a plurality of excitation beams 191-194. The scattered photons can be captured at the same time by a detector chip in such a way that the individual spectra remain differentiable. For example, acquisition of the Raman scattered light can take place in that the signals of different biological objects are acquired on a camera chip in different image lines and/or image columns of the camera chip and then sequentially read out.

Figure 27:
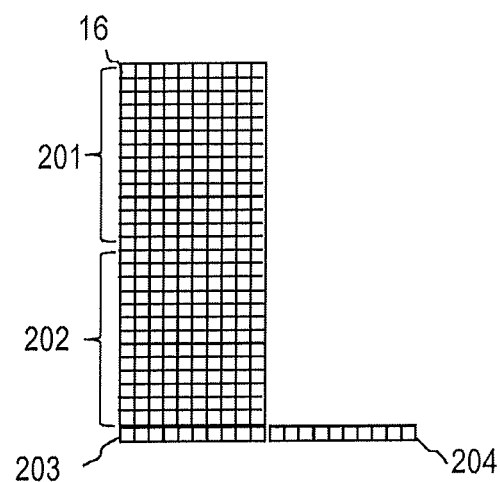
FIG. 27 shows a detector of a Raman spectroscopy system according to an example.

FIG. 27 shows a camera chip of the detector of the Raman spectroscopy system that can be used in order to acquire the Raman scattered light of a plurality of biological objects. The camera chip 16 can be an EMCCD (electron-multiplying charge-coupled device).

The camera chip 16 can be configured to carry out multiplication of image signals, also referred to as on-chip multiplication. The camera chip 16 can comprise one or a plurality of registers 181 for the acquisition of Raman scattered light. The camera chip 16 can optionally comprise one or a plurality of registers 182 for interim storage of acquired spectra. The camera chip 16 can comprise at least one readout register 183.

The camera chip 16 can be configured to shift the charges of different sensor lines at least for reading out in adjacent sensor lines.

The camera chip 16 can comprise a multiplication register 184. Amplification of the charges acquired in the readout register 183 can take place in the multiplication register 184. For this purpose, for example, an amplification process known in the art as a "clock-induced charge" or "spurious charge" can be used.

By means of the image acquisition in combination with shifting of the charges between sensor lines and multiplication in the camera chip 16, filtering can be achieved in the local or Fourier space by means of which the Raman scattered light signals from different biological traps can be differentiated.

Figure 28:
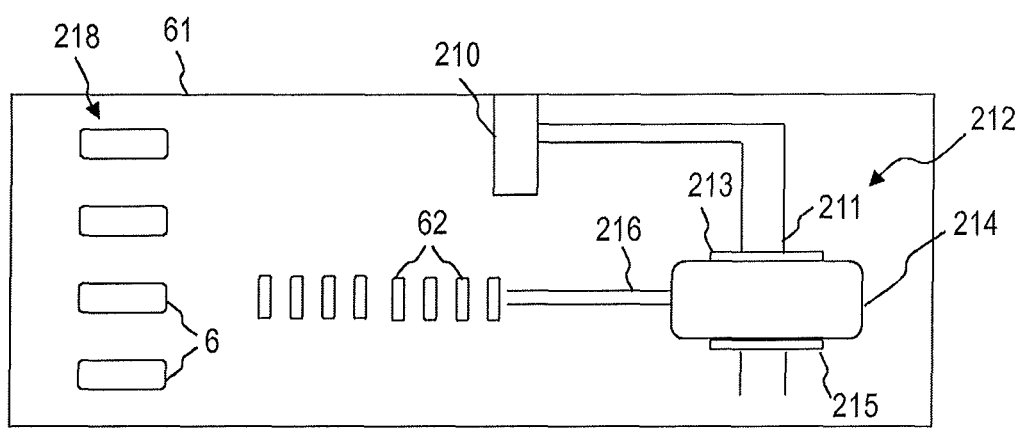
FIG. 28 shows a schematic top view of an arresting unit of a device according to an example.

FIG. 28 shows a top view of a configuration of an arresting unit 61 of a device according to an example. The arresting unit 61 can be configured as a microfluidic chip.

The arresting unit 61 can comprise a device 212 for the concentration of components of the sample. The device 212 can be configured to selectively concentrate one or a plurality of cellular or other components of the sample. For this purpose, osmotic effects can be used. At least one membrane 213, 215 can be used that has differing permeability for at least two different types of biological objects. For example, each of the membranes 213, 215 can show a different permeability for cellular blood components and for contaminants such as bacteria, fungi, yeasts, viruses or other contaminants.

At least one partial volume of a sample can be supplied for concentration via an inlet channel 210 and a connecting channel 211 of the device 212.

The device 212 for concentration comprises at least one element 213 showing a permeability for specified cells such as blood cells that differs from its permeability for microbes, bacteria or other contaminants. For example, the element 213 can be configured such that it shows higher permeability for cellular blood components than for bacteria. The element 213 can be a membrane. The element 213 can be flowed through by the partial volume of the sample so that because of the selective permeability, native cells or contaminants are concentrated in an area 214 of the arresting unit 61.

The arresting unit 61 can also comprise at least one further membrane 215 for concentration purposes. The at least one further membrane 215 can be configured such that its permeability for specified cells, for example, blood cells, differs from its permeability for microbes, bacteria or other contaminants.

From the area 214 in which the biological objects of one type or a plurality of different types are concentrated, the concentrated biological objects can be supplied via at least one connecting channel 216 in a fluid stream to one or a plurality of receptacle areas 62. In the one or a plurality of receptacle areas 62, the biological objects can be deposited by the effect of gravity or can be drawn into the recesses using optical or other electromagnetic radiation fields. In the receptacle areas 62, the biological objects can be subjected to Raman spectroscopy. In this context, at least one Raman spectrum can be acquired before administration of a substance and at least one further Raman spectrum can be acquired during or after administration of the substance respectively.

The biological objects can be supplied to a plurality 218 of collection receptacle areas 6. For this purpose, in accordance with the result of the Raman spectroscopy, biological objects can be selectively transferred into a fluid stream that flows over the receptacle areas 62 and at least one of the collection receptacle areas 6. The transfer can be carried out using optical tweezers or by means of other optical or electromagnetic radiation fields.

The fluid stream between the receptacle areas 62 and the collection receptacle areas 6 can be modified in a time-dependent manner. For example, the direction of the fluid stream can be controlled such that different collection receptacle areas 6 are flowed over by the fluid stream in a time-sequential manner. Depending on the collection receptacle area 6 to which a biological object is to be transferred based on its Raman spectra before and after administration of a substance, the point in time can be determined at which the biological objects are transferred from the receptacle areas 62 into the fluid stream that transports them to the desired collection receptacle area 6.

Figure 29:
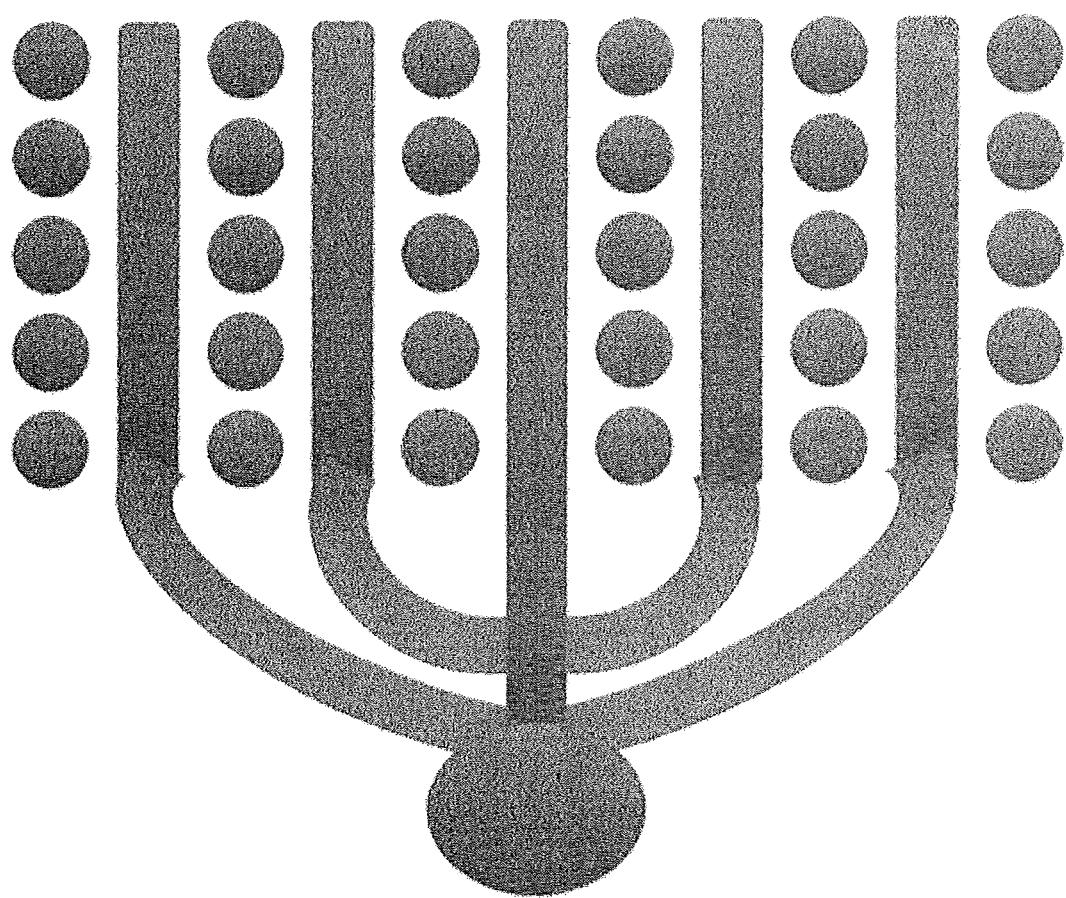
FIG. 29 shows an arresting unit that comprises microwells for receiving biological objects in a branching configuration with inlet or outlet channels. In this embodiment, biological objects can be moved as needed into one of the channels, transferred away from said channel, collected in an area, and sorted in this manner.
Figure 30:
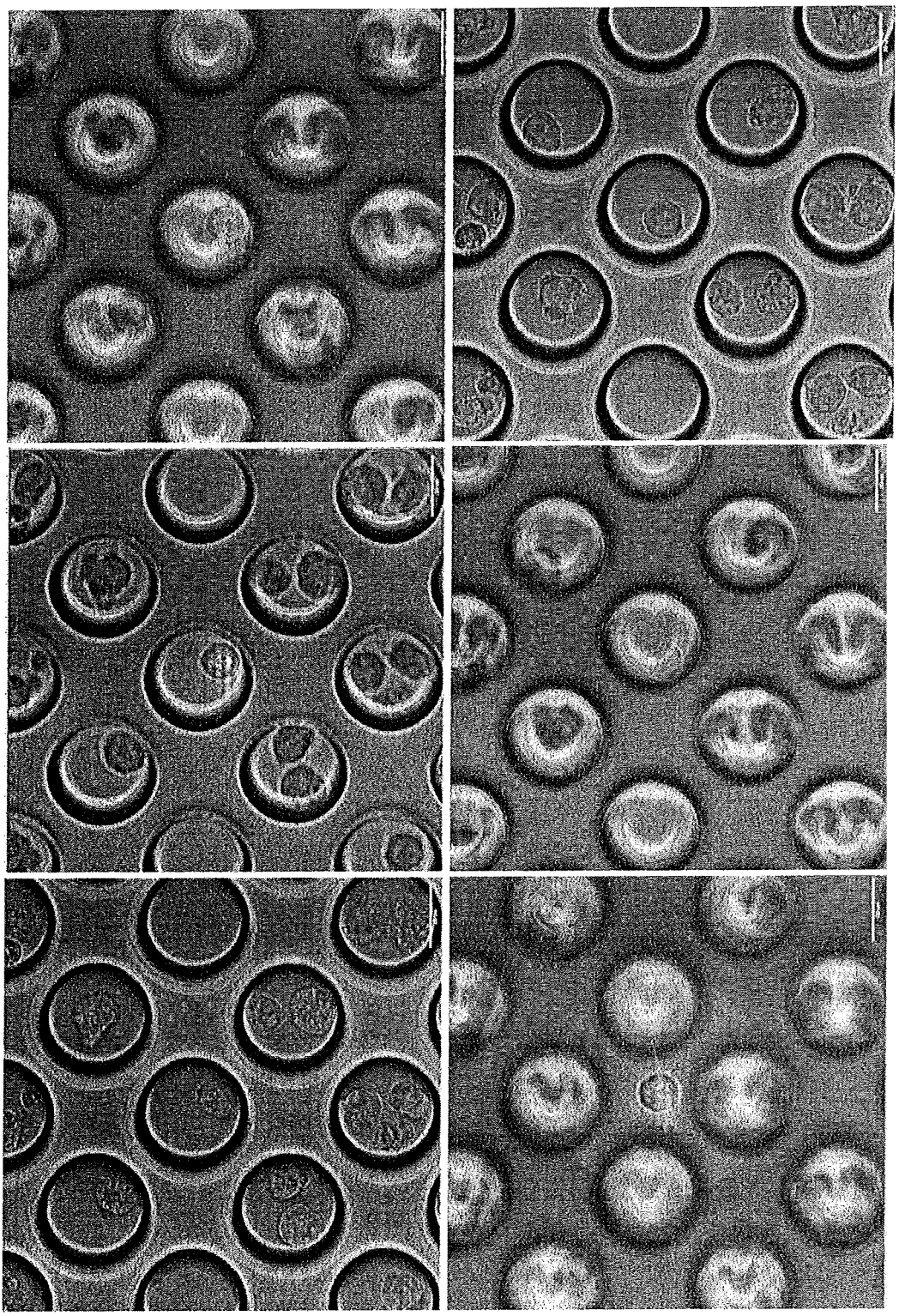
FIG. 30 shows microwells as parts of a microwell plate in different analysis stages. The microwells contain biological objects that are exposed to active substances.
Figure 14:
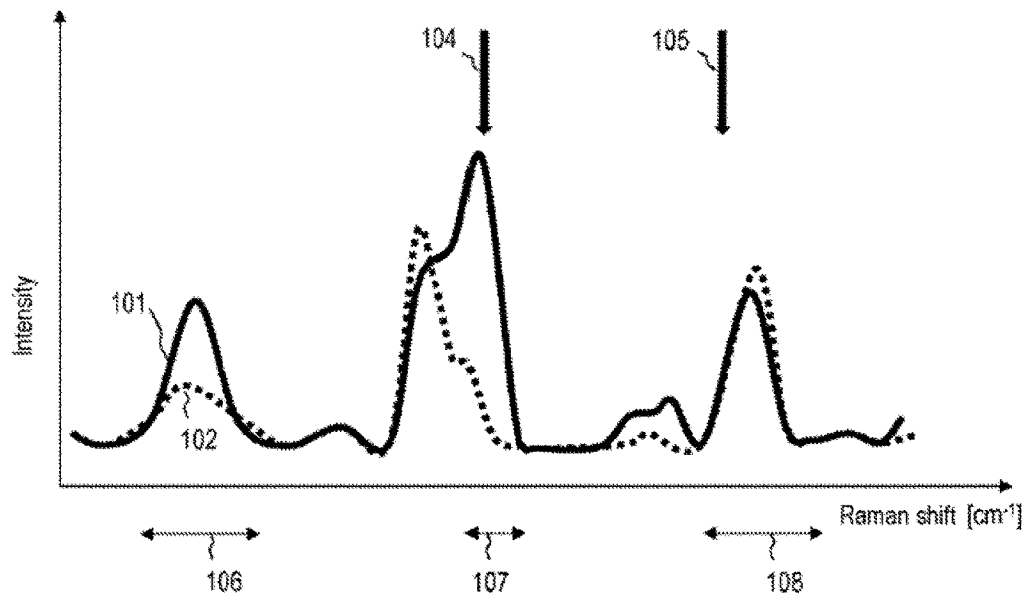
Figure 15:
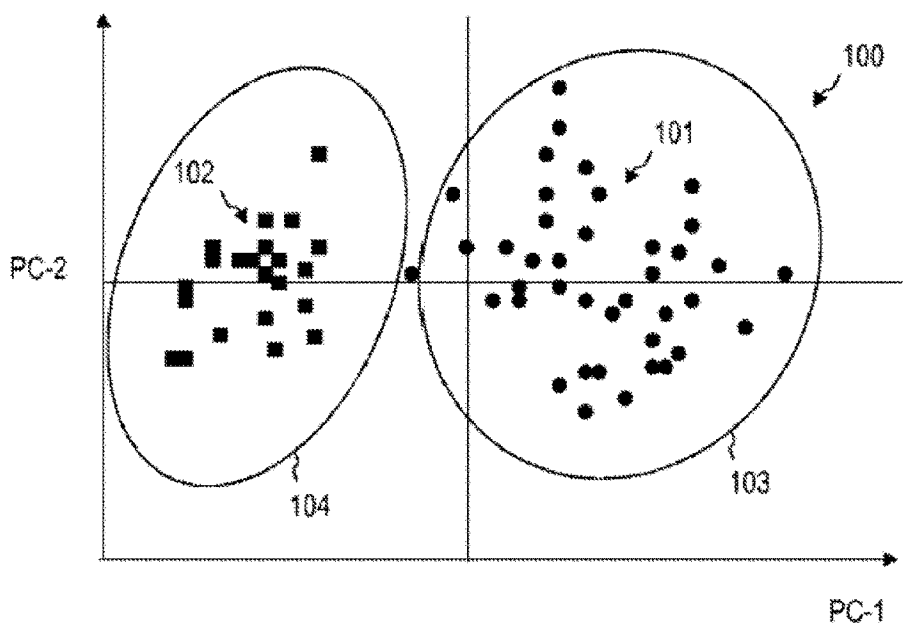
Figure 18:
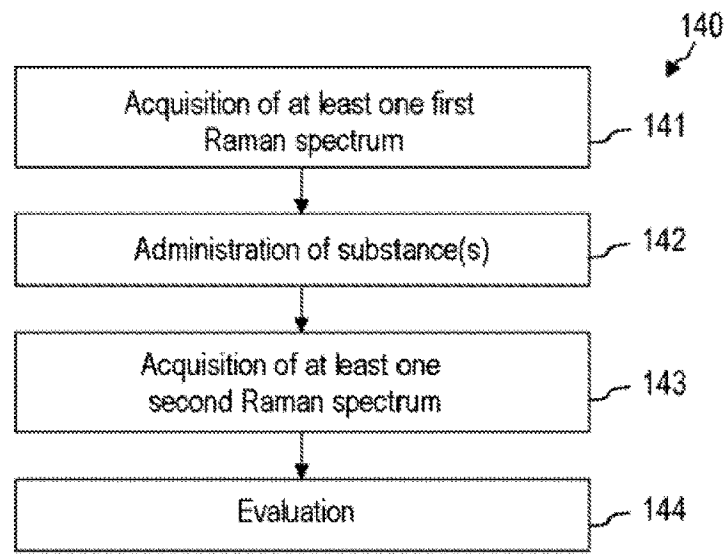
Figure 19:
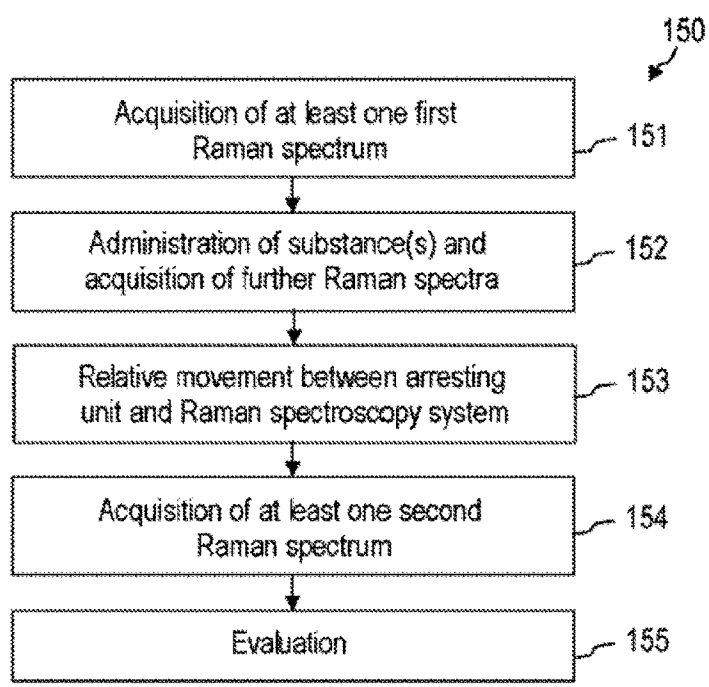
Figure 20:
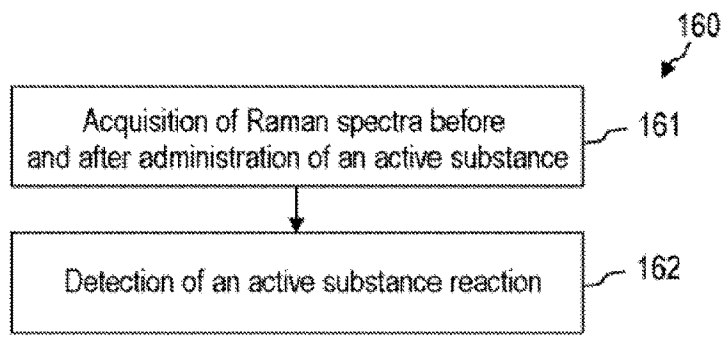
Figure 21:
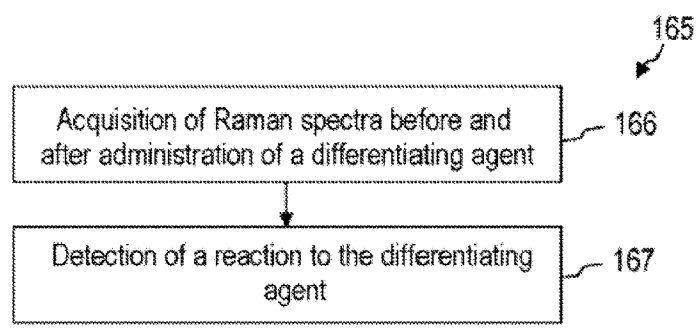
Figure 22:
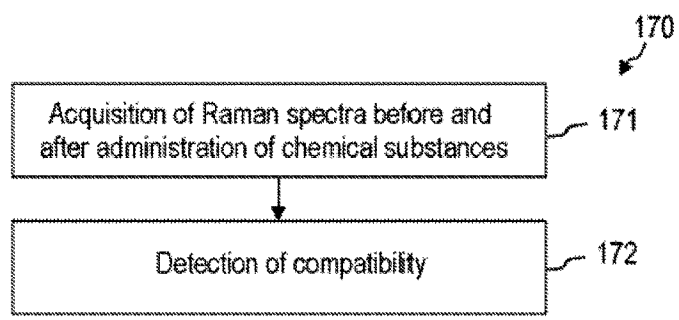
Figure 23:
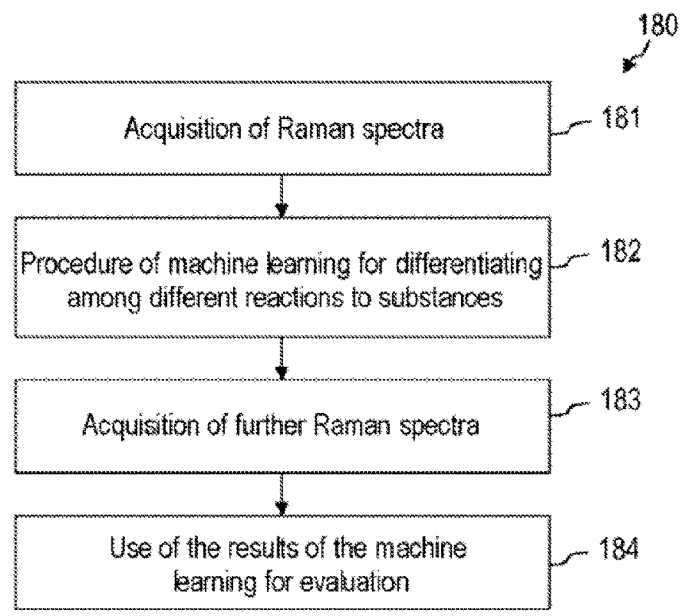
Figure 24:
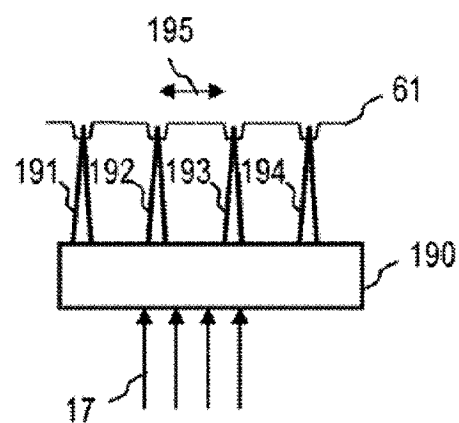

FIG. 29 shows a top view of a configuration of an arresting unit of a device according to an example. The arresting unit can comprise receptacle areas that are configured as microwells for accommodating biological objects. The receptacle areas can be arranged along channels carrying fluid flows. For this purpose, in accordance for example with a result of the Raman spectroscopy, biological objects can be selectively transferred into a fluid stream. The transfer can be carried out using optical tweezers or by means of other optical or electromagnetic radiation fields.

The arrangement of the channels can follow a hierarchical pattern, with a main branch and one or a plurality of auxiliary branches that can branch off at different locations on the main branch. The arrangement can further comprise a collection receptacle area into which all of the branches open directly or indirectly via the main branch. In addition, further subbranches may be present at all positions. The arrangement of the receptacle areas in the arresting unit makes it possible to automatically test a plurality of biological objects. The number of objects that can be tested simultaneously can be between 1 and 1,000. For example, 10, 20, 30, 40, 50, 100 or more biological objects can be tested simultaneously or also with a time lag. Moreover, it is possible to supply substances to all of the areas. Either the substances can be identical or different substances can be brought into the receptacle areas. Moreover, different sectors of the receptacle areas can be provided with different substances.

The branched arrangement of the receptacle areas in the arresting unit further makes it possible to transfer specified biological objects from the receptacle areas into the channels and thus sort them according to test results or any other logic. A group of biological objects, which for example have shown similar reactions to substances as described above, can thus be transported into a collection receptacle area so that they can be collected in said area, and optionally separated, subjected to further tests, or subjected to cultivation or expansion. Alternatively, the arrangement can also be used for the removal of biological objects that are no longer needed, for example because they have failed to meet test parameters. These biological objects can first be brought into a collection receptacle area and then disposed of.

The arresting unit, which comprises microwells for accommodating biological objects in a branched configuration with inlet or outlet channels, thus makes it possible to move biological objects as needed into one of the channels, where they are transported away and sorted.

Alternatively, a biological object can be transported from the collection receptacle area by means of a fluid stream, which is controllable, in the direction of specific receptacle areas or receptacles. At said location, it can be flushed in by means of a fluid stream or be carried into the receptacle, i.e. a microwell, using optical tweezers or by means of other optical or electromagnetic radiation fields. Inside the microwell, a biological object can then be deposited, for example under the action of gravity. Biological samples can also be again transported out according to the above-mentioned embodiments.

The devices and methods according to the examples as described herein can be used for testing a plurality of different biological objects and/or a plurality of different substances. For example, the devices and methods according to the examples can be used to identify suitable active substances in an automatic or computer-aided manner in order to develop personalized treatments in an automatic or computer-aided manner, or in order to automatically assess the compatibility of substances, for example for use in cosmetics.

The devices and methods according to the examples can generally be used for the quantitative testing of biological objects that are at least temporarily arrested by an arresting unit.

The invention claimed is:

1. A device for analyzing living cells or cell clusters, comprising
 a Raman spectroscopy system for acquiring at least one Raman spectrum,
 an arresting unit that is configured to at least temporarily arrest a living cell with an optical trap, and
 an electronic computing unit that is configured to determine a reaction of the cell arrested by the arresting unit to at least one substance in accordance with an evaluation of the at least one Raman spectrum.

2. The device as claimed in claim 1, wherein the device is configured to repeatedly engage the cell arrested by the arresting unit in order to acquire the at least one Raman spectrum.

3. The device as claimed in claim 1, comprising
 an actuator controllable by the electronic computing unit for producing a relative movement between the arresting unit and the Raman spectroscopy system.

4. The device as claimed in claim 3, wherein the electronic computing unit is configured to control the actuator in accordance with distances between at least two cells arrested by the arresting unit.

5. The device as claimed in claim 3, comprising
 an image acquisition device coupled to the electronic computing unit that is configured to acquire an image of the cell arrested by the arresting unit,
 wherein the electronic computing unit is configured to control the actuator in accordance with the acquired image.

6. The device as claimed in claim 5, wherein the image acquisition device comprises an optical path separate from a lens of the Raman spectroscopy system.

7. The device as claimed in claim 1, wherein the arresting unit comprises holding areas at each of which at least one cell is arrestable.

8. The device as claimed in claim 7, wherein the device is configured to produce a fluid stream flowing over the plurality of holding areas.

9. The device as claimed in claim 8, comprising
 a source of electromagnetic radiation that is configured to move the at least one cell from the fluid stream to a holding area and/or from the holding area into the fluid stream.

10. The device as claimed in claim 9, wherein the source of electromagnetic radiation comprises optical tweezers.

11. The device as claimed in claim 7, wherein each of the holding areas is dimensioned such that only exactly one cell is arrestable at each holding area.

12. The device as claimed in claim 7, wherein each of the holding areas is dimensioned such that a plurality of cells are arrestable at each of the holding areas.

13. The device as claimed in claim 1, comprising
 a supply unit for supplying the at least one substance to the cell.

14. The device as claimed in claim 13, wherein the electronic computing unit is configured, in accordance with the evaluation of the at least one Raman spectrum, to determine the reaction to a plurality of substances and/or, in accordance with the evaluation of a plurality of Raman spectra, to follow a course of the reaction in a time-dependent manner.

15. The device as claimed in claim 1, wherein the electronic computing unit is configured to detect a drug resistance in accordance with the evaluation of the at least one Raman spectrum.

16. The device as claimed in claim 15, wherein the electronic computing unit is configured, in order to detect the drug resistance, to compare a first Raman spectrum acquired before the supply of the at least one substance with a second Raman spectrum acquired after administration of an active substance.

17. The device as claimed in claim 1, wherein the at least one substance comprises an active substance, a toxin and/or a chemical.

18. The device as claimed in claim 1, wherein the at least one Raman spectrum evaluated by the electronic computing unit is acquired by Raman scattering on the cell.

19. The device as claimed in claim 1, wherein the at least one Raman spectrum evaluated by the electronic computing unit is acquired by Raman scattering on a material different from the cell.

20. The device as claimed in claim 1, wherein the device is configured to determine in parallel the reaction of a plurality of cells to a substance or a plurality of substances, wherein the device is configured to split an excitation beam of the Raman spectroscopy system in order to produce a plurality of electromagnetic beams for holding the plurality of cells and for Raman spectroscopy.

21. The device as claimed in claim 1, wherein the device is configured, in accordance with an evaluation of the at least one Raman spectrum of the cell arrested by the arresting unit, to selectively remove and/or sort said cell.

22. A method for analyzing living cells or cell clusters, comprising:
    arresting a living cell with an optical trap,
    acquiring at least one Raman spectrum of the arrested cell, and
    evaluating the at least one Raman spectrum in order to determine a reaction of the cell to at least one substance.

23. The method as claimed in claim 22, wherein the at least one substance comprises an active substance, a toxin and/or a chemical.

24. The method as claimed in claim 22, which is automatically carried out by a device for analyzing living cells or cell clusters comprising:
    a Raman spectroscopy system for acquiring at least one Raman spectrum,
    an arresting unit that is configured to at least temporarily arrest the cell with the optical trap, and
    an electronic computing unit that is configured to determine a reaction of the cell arrested by the arresting unit to at least one substance in accordance with an evaluation of the at least one Raman spectrum.

25. A method for analyzing living cells or cell clusters, comprising:
    arresting a living cell with an optical trap,
    acquiring at least one Raman spectrum of the arrested cell, and
    evaluating the at least one Raman spectrum in order to determine a reaction of the cell to at least one substance, wherein after evaluation of the at least one Raman spectrum in order to determine a reaction of the cell to at least one substance, the cell is selectively removed and/or sorted.

* * * * *

UNITED STATES PATENT AND TRADEMARK OFFICE
CERTIFICATE OF CORRECTION

PATENT NO. : 10,545,091 B2
APPLICATION NO. : 15/778116
DATED : January 28, 2020
INVENTOR(S) : Karin Schütze and Raimund Schütze It is certified that error appears in the above-identified patent and that said Letters Patent is hereby corrected as shown below:

In the Drawings

Several drawings include German text and are replaced with drawings that include English text:
Delete FIG. 14 and replace with attached FIG. 14
Delete FIG. 15 and replace with attached FIG. 15
Delete FIG. 18 and replace with attached FIG. 18
Delete FIG. 19 and replace with attached FIG. 19
Delete FIG. 20 and replace with attached FIG. 20
Delete FIG. 21 and replace with attached FIG. 21
Delete FIG. 22 and replace with attached FIG. 22
Delete FIG. 23 and replace with attached FIG. 23
Delete FIG. 24 and replace with attached FIG. 24

Signed and Sealed this
Sixth Day of July, 2021

Drew Hirshfeld
*Performing the Functions and Duties of the
Under Secretary of Commerce for Intellectual Property and
Director of the United States Patent and Trademark Office*